US010993658B2

(12) United States Patent
Wekell

(10) Patent No.: US 10,993,658 B2
(45) Date of Patent: *May 4, 2021

(54) SYSTEM AND METHOD FOR PATIENT MONITORING

(71) Applicant: BODIGUIDE INC., Bellevue, WA (US)

(72) Inventor: William Oren Wekell, Maple Valley, WA (US)

(73) Assignee: BODIGUIDE INC., Belllevue, WA (US)

(*) Notice: Subject to any disclaimer, the term of this patent is extended or adjusted under 35 U.S.C. 154(b) by 1240 days.

This patent is subject to a terminal disclaimer.

(21) Appl. No.: 14/481,742

(22) Filed: Sep. 9, 2014

(65) Prior Publication Data

US 2014/0378785 A1 Dec. 25, 2014

Related U.S. Application Data

(63) Continuation of application No. 12/987,985, filed on Jan. 10, 2011, now Pat. No. 8,827,930.

(51) Int. Cl.
*A61B 5/00* (2006.01)
*A61B 5/107* (2006.01)
(Continued)

(52) U.S. Cl.
CPC .......... *A61B 5/4878* (2013.01); *A61B 5/0002* (2013.01); *A61B 5/0004* (2013.01);
(Continued)

(58) Field of Classification Search
CPC ... A61B 5/4878; A61B 5/4848; A61B 5/7275; A61B 5/1072; A61B 5/742;
(Continued)

(56) References Cited

U.S. PATENT DOCUMENTS 492,973 A 3/1893 Shepard
3,853,118 A * 12/1974 Schendel ............... A61B 5/107
600/595

(Continued)

FOREIGN PATENT DOCUMENTS

WO 8909566 A1 10/1989
WO 2009125327 A1 10/2009

OTHER PUBLICATIONS

Abdalla dos Reis, et al., "Analysis of the Figure-of-Eight Method and Volumetry Reliability for Ankle Edema Measurement," Revista Brasileira de Medicinia do Esporte, Nov. 2004, published online at http://www.sciela.br/scielo.php?pid=S1517-869220040006000038&script=sci_arttext&tlng=en, 8 pages.

(Continued)

*Primary Examiner* — Sean P Dougherty
(74) *Attorney, Agent, or Firm* — Han Santos, PLLC; Gloria M. Steinberg

(57) ABSTRACT

Systems and methods of monitoring a patient. Exemplary methods include receiving sensor data associated with the patient from a plurality of sensors of a patient monitoring device and determining whether the sensor data satisfies one or more trigger conditions. For each of the trigger conditions satisfied, one or more messages are sent to at least one of the patient monitoring device and an external computing device for display thereby to at least one of the patient, a caregiver, and a support person. Satisfaction of one or more of the trigger conditions may indicate the patient has edema and/or is trending toward decompensation. The sensor data may have been collected from a heart rate sensor, an oximeter, an accelerometer, and/or a sensor configured to detect a distance around a limb of a patient. In some embodiments, the trigger conditions are provided by the patient, caregiver, and/or support person.

20 Claims, 17 Drawing Sheets

(51) Int. Cl.
*A61B 5/0205* (2006.01)
*A61B 5/11* (2006.01)
*A61B 5/145* (2006.01)
*A61B 5/024* (2006.01)

(52) U.S. Cl.
CPC .......... *A61B 5/0022* (2013.01); *A61B 5/0205* (2013.01); *A61B 5/107* (2013.01); *A61B 5/1072* (2013.01); *A61B 5/1118* (2013.01); *A61B 5/14542* (2013.01); *A61B 5/486* (2013.01); *A61B 5/4839* (2013.01); *A61B 5/4848* (2013.01); *A61B 5/6831* (2013.01); *A61B 5/7275* (2013.01); *A61B 5/7282* (2013.01); *A61B 5/742* (2013.01); *A61B 5/747* (2013.01); *A61B 5/7475* (2013.01); *A61B 5/024* (2013.01); *A61B 5/1073* (2013.01); *A61B 5/1075* (2013.01); *A61B 5/1077* (2013.01); *A61B 5/1107* (2013.01); *A61B 5/6824* (2013.01); *A61B 5/6828* (2013.01)

(58) Field of Classification Search
CPC ..... A61B 5/4839; A61B 5/107; A61B 5/1073; A61B 5/1075; A61B 5/1107; A61B 5/1077; A61B 5/6824; A61B 5/6828
See application file for complete search history.

(56) References Cited

U.S. PATENT DOCUMENTS

| | | | |
|---|---|---|---|
| 4,635,367 A | 1/1987 | Vigede | |
| 4,658,632 A | 4/1987 | Sasaki | |
| 4,658,832 A | 4/1987 | Brugnoli | |
| 4,715,235 A | 12/1987 | Fukui et al. | |
| 4,852,582 A | 8/1989 | Pell | |
| 4,884,460 A | 12/1989 | Nowacki et al. | |
| 4,944,306 A | 7/1990 | Alvino | |
| 5,016,636 A | 5/1991 | Kulakowski | |
| 5,191,893 A | 3/1993 | Reiten | |
| 5,277,195 A | 1/1994 | Williams | |
| 5,284,133 A | 2/1994 | Burns et al. | |
| 5,339,825 A | 8/1994 | McNaughton et al. | |
| 5,363,842 A | 11/1994 | Mishelevich et al. | |
| 5,415,176 A | 5/1995 | Sato et al. | |
| 5,469,750 A | 11/1995 | Lloyd et al. | |
| 5,497,787 A * | 3/1996 | Nemesdy | A61B 5/107 600/507 |
| 5,522,380 A | 6/1996 | Dwork | |
| 5,676,129 A | 10/1997 | Rocci, Jr. et al. | |
| 5,704,366 A | 1/1998 | Tacklind et al. | |
| 5,724,986 A | 3/1998 | Jones, Jr. et al. | |
| 5,769,070 A | 6/1998 | Frati et al. | |
| 5,785,048 A | 7/1998 | Koerner | |
| 5,788,643 A | 8/1998 | Feldman | |
| 5,804,963 A | 9/1998 | Meyer | |
| 5,839,430 A | 11/1998 | Cama | |
| 5,891,059 A | 4/1999 | Anderson | |
| 5,915,386 A | 6/1999 | Lloyd et al. | |
| 5,916,183 A | 6/1999 | Reid | |
| 6,014,080 A | 1/2000 | Layson, Jr. | |
| 6,039,688 A | 3/2000 | Douglas et al. | |
| 6,077,222 A | 6/2000 | Lloyd et al. | |
| 6,077,224 A | 6/2000 | Lang et al. | |
| 6,189,538 B1 | 2/2001 | Thorpe | |
| 6,190,326 B1 | 2/2001 | McKinnon et al. | |
| 6,261,230 B1 * | 7/2001 | Bardy | A61B 5/0031 600/300 |
| 6,270,457 B1 | 8/2001 | Bardy | |
| 6,285,757 B1 | 9/2001 | Carroll et al. | |
| 6,322,519 B1 | 11/2001 | Moulin | |
| 6,358,058 B1 | 3/2002 | Strupat et al. | |
| 6,416,471 B1 | 7/2002 | Kumar et al. | |
| 6,440,066 B1 * | 8/2002 | Bardy | A61B 5/0002 600/300 |
| 6,447,459 B1 | 9/2002 | Larom | |
| 6,461,307 B1 | 10/2002 | Kristbjamarson et al. | |
| 6,526,315 B1 | 2/2003 | Inagawa et al. | |
| 6,600,949 B1 | 7/2003 | Turcott | |
| 6,602,191 B2 | 8/2003 | Quy | |
| 6,679,250 B2 | 1/2004 | Walker et al. | |
| 6,773,404 B2 | 8/2004 | Poezevera et al. | |
| 6,829,503 B2 | 12/2004 | Alt | |
| 6,970,731 B1 | 11/2005 | Jayaraman et al. | |
| 7,063,669 B2 | 6/2006 | Brawner et al. | |
| 7,156,809 B2 | 1/2007 | Quy | |
| 7,185,650 B2 | 3/2007 | Huber et al. | |
| 7,201,726 B2 | 4/2007 | Vastano | |
| 7,353,179 B2 | 4/2008 | Ott et al. | |
| 7,384,395 B2 | 6/2008 | Hatlestsad et al. | |
| 7,484,408 B2 | 2/2009 | Healey | |
| 7,867,172 B1 | 1/2011 | Baruti et al. | |
| 7,867,185 B2 | 1/2011 | Lipshaw | |
| 8,142,369 B2 | 3/2012 | Sanders et al. | |
| 8,500,659 B2 * | 8/2013 | Vastano | A61B 5/1073 600/587 |
| 2002/0124295 A1 | 9/2002 | Fenwick et al. | |
| 2003/0055461 A1 | 3/2003 | Girouard et al. | |
| 2004/0034294 A1 | 2/2004 | Kimball et al. | |
| 2004/0039261 A1 * | 2/2004 | Bardy | A61B 5/0006 600/300 |
| 2004/0144076 A1 * | 7/2004 | Barker | A44C 15/00 59/1 |
| 2004/0186395 A1 * | 9/2004 | Vastano | A61B 5/1073 600/587 |
| 2005/0090754 A1 | 4/2005 | Wolff et al. | |
| 2005/0119777 A1 * | 6/2005 | Arbogast | A61F 2/7812 700/117 |
| 2005/0159690 A1 * | 7/2005 | Barak | A61H 9/0078 601/149 |
| 2005/0177061 A1 | 8/2005 | Alanen et al. | |
| 2005/0234352 A1 | 10/2005 | Bardy | |
| 2006/0017575 A1 * | 1/2006 | McAdams | A61B 5/0031 340/573.1 |
| 2006/0036134 A1 | 2/2006 | Tarassenko et al. | |
| 2006/0122540 A1 | 6/2006 | Zhu et al. | |
| 2007/0016019 A1 * | 1/2007 | Salgo | A61B 8/0883 600/437 |
| 2007/0135737 A1 * | 6/2007 | Vastano | A61B 5/1073 600/587 |
| 2007/0293738 A1 | 12/2007 | Bardy | |
| 2007/0293741 A1 | 12/2007 | Bardy | |
| 2008/0000304 A1 | 1/2008 | Nagle et al. | |
| 2008/0146961 A1 * | 6/2008 | Okura | A61B 5/107 600/547 |
| 2008/0249441 A1 | 10/2008 | Avitable et al. | |
| 2009/0151718 A1 | 6/2009 | Hunter et al. | |
| 2009/0156908 A1 | 6/2009 | Belalcazar et al. | |
| 2009/0234262 A1 * | 9/2009 | Reid, Jr. | A61B 5/026 601/152 |
| 2009/0270751 A1 | 10/2009 | Peng et al. | |
| 2010/0004563 A1 | 1/2010 | Lipshaw | |
| 2010/0094099 A1 | 4/2010 | Levy et al. | |
| 2011/0067623 A1 * | 3/2011 | Fagan | G09F 11/23 116/201 |
| 2011/0245711 A1 * | 10/2011 | Katra | A61B 5/0537 600/547 |
| 2012/0004603 A1 * | 1/2012 | Harari | A61B 5/1075 604/74 |
| 2013/0121461 A1 * | 5/2013 | Toll | A61B 5/1072 378/53 |

OTHER PUBLICATIONS

Adamson, et al., "Continuous Autonomic Assessment in Patients with Symptomatic Heart Failure: Prognostic Value of Heart Rate Variability Measured by an Implanted Cardiac Resynchronization Device," Circulation, Oct. 19, 2004, pp. 2389-2394.

Agency for Healthcare Research and Quality, "Preventable Hospitalizations: A Window Into Primary and Preventative care, 2000," HCUP Fact Book No. 5, AHRQ Publication No. 04-0056, Sep. 2004, 64 pages.

(56) References Cited

OTHER PUBLICATIONS

Akosah, et al., "Improving Care for Patients with Chronic Heart Failure in the Community," Chest 122, American College of Chest Physicians, 2002 pp. 906-912. 5.
Blair, et al., "Weight Changes After Hospitalization for Worsening Heart Failure and Subsequent Re-Hospitalization and Mortality in the EVEREST Trail," European heart Journal 30, 2009, pp. 1666-1673.
Bogert and Lieshout, "Non-Invasive Pulsatile Arterial Pressure and Stroke Volume Changes from the Human Finger," Experimental Physiology 90(4),2005, pp. 437-446.
Braunschweig, et al., "Can Monitoring of Intrathoracic Impedance Reduce Morbidity and Mortality in Patients with Chronic Heart Failure? Rationale and Design of the Diagnostic Outcome Trail in Heart Failure (DOT-HF)," European Journal of Heart Failure 10,2008, pp. 907-916.
Brodovicz, et al., "Reliability and Feasibility of Methods to Quantitatively Assess Peripheral Edema," Clinical Medicine & Research 7(1-2), Feb. 26, 2009, pp. 21-31.
Chakko, et al., "Clinical, Radiographic, and Hemodynamic Correlations in Chronic Congestive Heart Failure: conflicting Results May Lead to Inappropriate Care," The American Journal of Medicine 90, Mar. 1991, pp. 353-359.
Chaudry, et al., "Telemonitoring for Patients With Chronic Heart Failure: A Systematic Review," Journal of Cardiac Failure 13(1), Feb. 2007, pp. 56-62.
Chin and Goldman, "Factors Contributing to the Hopitalization of Patients with Congestive Heart Failure," American Journal of Public Health, 87(4), Apr. 1997, pp. 643-648.
Cornish, et al., "A New Technique for the Quantification of Peripheral Edema with the Application in Both Unilateral and Bilateral Cases," Angiology 53(1), 2002, pp. 41-47, downloaded at http://ang.sagepub.com/cgi/content/abstract/53/1/41 on Aug. 28, 2009.
Cotter, et al., "Fluid Overload in Acute Heart Failure—Redistribution and Other Mechanisms Beyond Fluid Accumulation," European Journal of Heart Failure 10,2008, pp. 165-169.
Davie, et al., "Assessing Diagnosis in Heart Failure: Which Features Are Any Use?" Quarterly Journal of Medicine 90, 1997, pp. 335-339.
Dickstein, et al., "ESC Guidelines for the Diagnosis and Treatment of Acute and Chronic Heart Failure 2008," European Heart Journal 29(19), 2008, pp. 2388-2442.
Dickstein, et al., "ESC Guidelines for the Diagnosis and Treatment of Acute and Chronic Heart Failure 2008," European Journal of Heart Failure, 2008, pp. 933-989.
Exmovere, LLC, "The New Biological Frontier: The Empath Watch," internal document on Research and Design Methods, published on or before Jul. 15, 2010, pp. 1-16.
Frankel, et al., "Validation of Prognostic Models Among Patients with Advanced Heart Failure," Journal of Cardiac Failure 12(6),2006, pp. 430-438.
Friedman, "Older Adults' Symptoms and Their Duration before Hospitalization for Heart Failure," Heart & Lung 26(3), May-Jun. 1997, pp. 169-176.
Gheorghiade, et al., "Acute Heart Failure Syndrome: Current State and Framework for Future Research," Circulation, American Heart Association, Dec. 20/27, 2005, pp. 3958-3968.
Goldberg, et al. "Randomized Trial of a Daily Electronic Home Monitoring System in Patients with Advanced Heart Failure: The Weight Monitoring in Heart Failure Trial," American Heart Journal, Oct. 2003, pp. 705-712.
Hastings, "Congestive Heart Failure," white paper, Jul. 6, 2004, pp. 1-9.
Henrick, "Cost-Effective Outpatient Management of Persons with Heart Failure," Progress in Cardiovascular Nursing, Spring 2001, pp. 50-56.
HFSA, "Module 4: Self-Care: Following Your Treatment Plan and Dealing with Your Symptoms," Heart Failure Society of America, St. Paul, MN, 2003,16 pages.
Hunt, et al., "2009 Focused Update Incorporation into the ACC/AHA 2005 Guidelines for the Diagnosis and management of Heart Failure in Adults: A Report of the American College of Cardiology Foundation/ American Heart Association Task Force on Practice Guidelines Developed in Collaboration with the International Society for Heart and Lung Transplantation," Journal of the American College of Cardiology 53,2009, pp. e1-e90.
Impedance Cardiography, "Impedance Cardiography: Technology, Validity, and Clinical Application," published on or before Aug. 13, 2009, 77 pages.
International Search Report dated Jan. 2, 2013, received in International Application No. PCT/US2012/020667, 4 pages.
International Search Report dated Jun. 25, 2012, received in International Application No. PCT/US2012/020666, 11 pages.
Karkas and Bozkir, "Determination of Normal Calf and Ankle Values Among Medical Students," Aesthetic Plastic Surgery 31,2007, pp. 179-182.
Khan, et al., "Functional Specification: Edema Measurement System," Vedo Medico, Feb. 20, 2006, 15 pages.
Kim, et al., "Prognostic Value of a Novel Classification Scheme for Heart Failure: The Minnesota Heart Failure Criteria," American Journal of Epidemiology 164, 2006, pp. 184-193.
Lee, et al., "Economic Burden of Heart Failure: A Summary of Recent Literature," Heart & Lung 33(6), Nov./Dec. 2004, pp. 362-371.
Lewin, et al., "clinical Deterioration in Established Heart Failure: What is the value of BNP and Weight Gain in Aiding Diagnosis?" The European Journal of Heart Failure 7, 2005, pp. 953-957.
Maric et al., "A Systematic Review of Telemonitoring Technologies in Heart Failure," European Journal of Heart Failure 11, 2009, pp. 506-517. EFS.
Medtronic, Inc., "Medtronic Kappa 900 Specification," downloaded from http://www.medtronic.com/crm/kappa900/specs.html, published 2004, 1 page.
Nicholaou, "Model Predictive Controllers: A Critical Synthesis of Theory and Industrial Needs," Advances in Chemical engineering 26, 2001, 50 pages.
Nike, Inc., "The Nike+ Sensor: Run tracking made easy," downloaded from http://store.nike.com/us/en_us/?1=shop, pdp,ctr-inline/cid-1/pid-162953/pgid-162953, published on or before Mar. 18, 2008,14 pages.
O'Connor, et al., "Demographics, Clinical Characteristics, and Outcomes of Patients Hospitalized for Decompensated Heart Failure: Observations from the MPACT-HF Registry," Journal of Cardiac Failure 11(3), 2005, pp. 200-205.
Opasich, et al., "Precipitating Factors and Decision Making Processes of Short-Term Worsening Heart failure Despite "Optimal" Treatment (from the IN-CHF Registry)," American Journal of Cardiology 88, Aug. 15, 2001, pp. 382-387.
Paul, "Hospital Discharge Education for Patients with Heart Failure: What Really Works and What is the Evidence?" Critical Care Nurse 28, 2008, published online at http://ccn.aacnjournals.org/cgi/contenUfuli/28/2/66, pp. 66-82.
Perrin and Guex, "Edema and Leg Volume: Methods of Assessment," Angiology The Journal of Vascular Disease 51 (1), Jan. 2000, pp. 9-12.
Qmed.com, Telehealth Market in Tight Competition Companies are Fighting for their Share of the Electronic Health Monitoring Business, Which is Expected to Grow 55% Annually Over the Next Five Years downloaded from http://www.qmed.com/news/25498/telehealth-market-tight-competition-companies-are-fighting-their-share-electronic-health (10/21/20109:11 :56 AM], CMP Media LLC, on Oct. 21, 2010,2 pages.
Rich and Nease, "Cost-effectiveness Analysis in Clinical Practice: The Case of Heart Failure," Archives of Internal Medicine 159, Aug. 9/23, 1999, pp. 1690-1700.
Rich, "Heart Failure Disease Management Programs: Efficacy and Limitations," American Journal of Medicine 110, 2001 pp. 410-412.
Ross, et al., "Statistical Models and Patient Predictors of Readmission for Heart Failure: a Systemic Review," Archives of internal Medicine 168(13), Jul. 14, 2008, pp. 1371-1386.

(56) References Cited

OTHER PUBLICATIONS

Schiff, et al., "Decompensated Heart Failure: Symptoms, Patterns of Onset, and Contributing Factors," The American Journal of Medicine 114, Jun. 1, 2003, pp. 625-630.

ScienceDaily LLC, "Cell Phones Manage Diabetes: Epidemiologists Use Wireless Technology to Improve Blood Sugar Monitoring," Sep. 1, 2008, downloaded from http://www.sciencedaily.com/videos/2008/0902-cell_phones_manage_diabetes.htm on Mar. 9, 2010, 2 pages.

Silver, "New Approaches to Hemodynamic Measurement: Cool Devices by a Shaky Infrastructure," Journal of American College of Cardiology 50, Dec. 11, 2007, published online at http://content.onlinejacc.org/cgi/content/full/50/25/2383, pp. 2383-2384.

Stevens, "Fitbit Review," downloaded from http://www.engadget.com/2009/10/15/fitbit-review.com, published on or before Oct. 15, 2009, 6 pages.

Stevenson, et al., "The Limited Reliability of Physical Signs for Estimating Hemodynamics in Chronic Heart Failure," Journal of the American Medical Association 261 (6), Feb. 10, 1989, pp. 884-888.

Trigano, et al., "Clinical Study of Interference with Cardiac Pacemakers by a Magnetic Field at Power Line Frequencies," Journal of the American College of Cardiology 45(6),2005, published online at http://content.onlinejacc.org/cg i/contenUfu 11/45/6/896, pp. 896-900.

Unknown, "Clinical Assessment and Investigation of Patients with Suspected Heart Failure: Use of Symptoms and Signs in Clinical Diagnosis," published on or before Jul. 31, 2009, pp. 76-79.

Unknown, "Edema Formation in Heart Failure," downloaded from http://stevetakeshisfirststep.wordpress.com/2008/03/21/edema-formation-in-heart-failure/ on Aug. 14, 2009, 5 pages.

Webel, et al., "Daily Variability in Dyspnea, Edema and Body Weight in Heart Failure Patients," Journal of Cardiovascular Nursing 6, 2007, pp. 60-65.

Wilkinson, et al., "Reproducibility of Pulse Wave Velocity and Augmentation Index Measured by Pulse Wave Analysis," Journal of Hypertension 16(12), Dec. 1998, pp. 2079-2084.

Wolfel, "Can We Predict and Prevent the Onset of Acute Decompensated Heart Failure?" Circulation 116, 2007, pp. 1526-1529.

Yu, et al., "Intrathoracic Impedance Monitoring in Patients With Heart Failure: Correlation With Fluid Status and Feasibility of Early Warning Preceding in Hospitalization," Circulation, American Heart Association, Aug. 9, 2005, pp. 841-848.

Zannad, et al., "Incidence, Clinical and Etiologic Features, and Outcomes of Advanced Chronic Heart Failure: the EPICAI Study," Journal of the American College of Cardiology, vol. 33, No. 3, Mar. 1, 1999, pp. 734-742.

U.S. Appl. No. 12/987,985, Final Office Action dated Nov. 4, 2013, 16 pages.

U.S. Appl. No. 12/987,985, Non-Final Office Action dated Jun. 10, 2013, 31 pages.

* cited by examiner

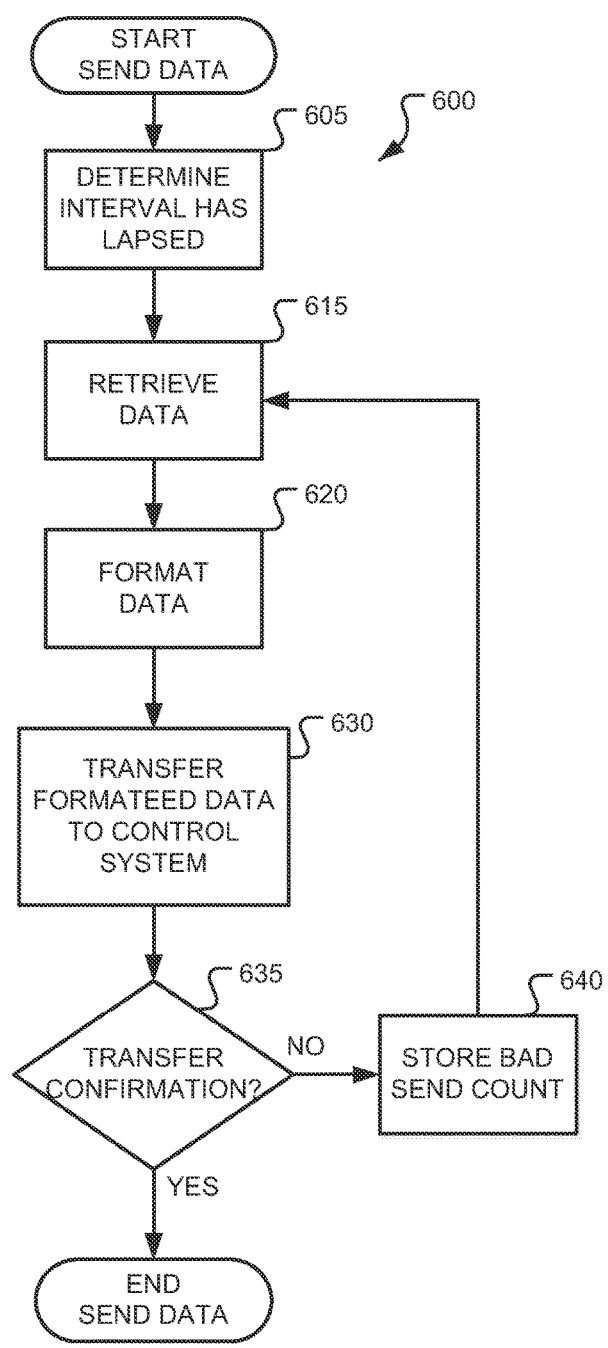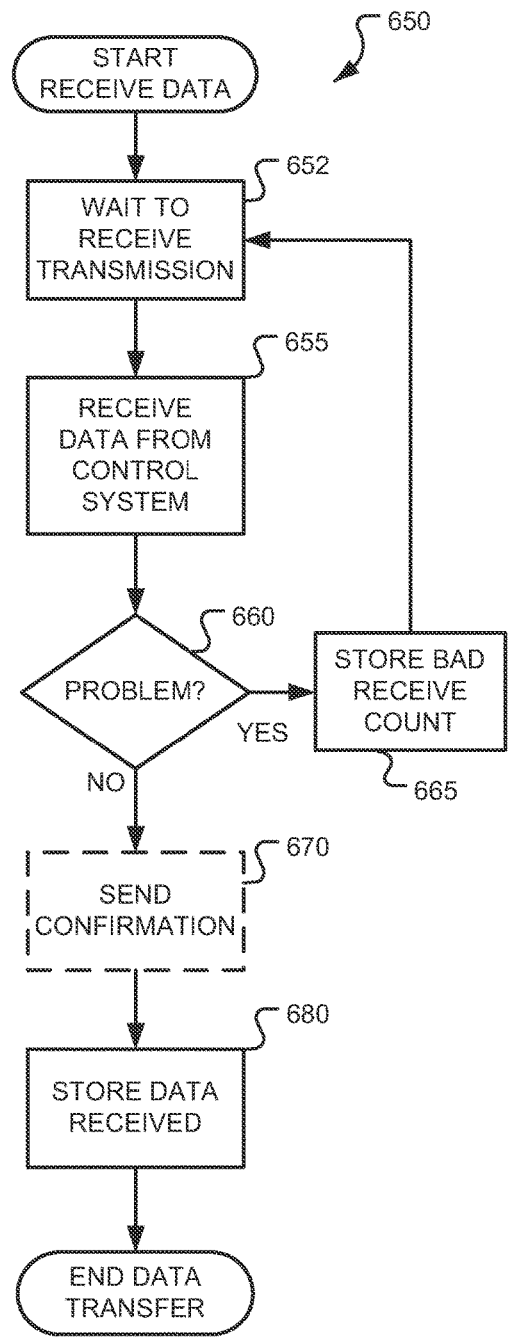
FIGURE 6A
FIGURE 6B

DETAIL B

SECTION A-A

SYSTEM AND METHOD FOR PATIENT MONITORING

BACKGROUND OF THE INVENTION

Field of the Invention

The present invention is directed generally to devices and methods for monitoring patient health, and more particularly, to methods and systems for detecting edema.

Description of the Related Art

Monitoring patient parameters is quite common in medical care environments, such as hospitals, doctors' offices, and the like. Further, patient monitoring outside of a clinical setting is increasing because of the rising cost of traditional healthcare. There is a need for devices configured to monitor a patient's health. Devices configured to notify professional healthcare providers when appropriate are particularly desirable.

A "compensated" system is able to function despite any stressors or defects that might be present. Decompensation occurs when the system can no longer compensate for these issues. Decompensation is a general term commonly used in medicine to describe a variety of situations.

Cells are surrounded by an extracellular fluid that includes interstitial fluid, plasma, and transcellular fluid. The interstitial fluid is found in the interstitial spaces, also known as the tissue spaces. Edema is an abnormal accumulation of fluid in the interstitial spaces that causes swelling.

Edema in the feet and legs is often referred to as peripheral edema. Limb volume changes have sufficient specificity and sensitivity to be predictive of impending heart failure decompensation in some forms of heart failure. The physiological conditions that cause an increase in interstitial fluid in the limbs of a heart failure patient may also cause decompensation. Therefore, edema may be predictive of congestive chest conditions that can endanger the patient.

There are several traditional methods of measuring or evaluating edema. The most commonly used method is to press a depression into the skin (e.g., of the lower leg) and assign a grade (e.g., on a 1 to 4 scale) indicating an amount of edema present based on the depth and persistence of the depression. This method provides a coarse but useful measure of edema.

More accurate methods of measuring or evaluating edema include placing the patient's limb in a container of water and measuring an amount of fluid displaced by the patient's limb. By collecting two or more displacement measurements, a change in limb volume, if any, that occurred between measurements can be determined. Unfortunately, this method is wet, cumbersome, and unsuitable for continuous patient monitoring and data collection.

A Leg-O-Meter device may be used to measure edema. The Leg-O-Meter device includes a tape measure positioned at a predetermined height above the floor. The tape measure is used to determine a single distance around a limb. While results obtained by the Leg-O-Meter device are well correlated with those obtained using the more cumbersome fluid displacement method, the Leg-O-Meter device requires a skilled practitioner to operate and the active involvement of the patient.

Electronic measurement devices also exist that are large, expensive, and fixed making them unsuitable for a home environment. Further, such devices typically do not provide methods of communicating with the patient, a caregiver, or a healthcare provider. These devices also do not typically analyze the data collected.

Quantifying and monitoring peripheral edema is important because the onset of edema and/or changes in an amount of edema present can occur many days prior to a considerable decline in patient health. In other words, the onset of edema and/or changes in an amount of edema present may predict (e.g., by several days) a significant decline in a patient's health. This predictive indication may be used in some cases to avoid a significant decline in patient health. For example, such early warning of an impending problem may be used to adjust the patient's diet, salt intake, medications, and the like. Further, consultation with healthcare professionals before the decline occurs may avoid precipitous health declines, such as, but not limited to, decompensated heart failure. Therefore, a need exists for methods and systems that provide substantially continuous monitoring of edema. A need also exists for methods and systems that track a patient's physiological parameters and symptoms for the purposes of detecting trends and/or recognizing impending patient health conditions that may require medical intervention, such as hospitalization.

The present application provides these and other advantages as will be apparent from the following detailed description and accompanying figures.

BRIEF DESCRIPTION OF THE SEVERAL VIEWS OF THE DRAWING(S)

FIG. 6A is a flow diagram of a method of transmitting the patient data collected to the control system.

FIG. 6B is a flow diagram of a method performed the device worn on a patient's limb when receiving messages and/or data from the control system.

DETAILED DESCRIPTION OF THE INVENTION

Overview

Figure 1:
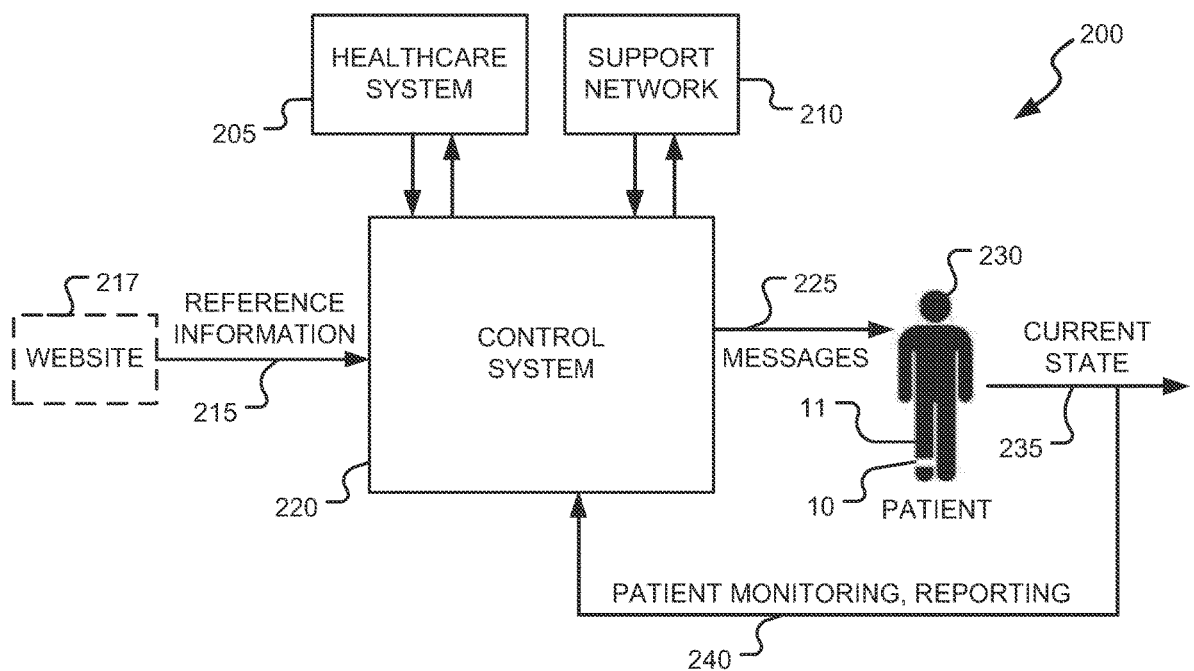
FIG. 1 is a diagram of a system configured to detect edema.

Referring to FIG. 1, the present application describes a system 200 that includes a device 10 worn by a patient 230 that is connected (e.g., wirelessly) to a control system 220. The control system 220 may be connected (e.g., wirelessly) to a healthcare system 205, a support network 210, and the like. The healthcare system 205 includes healthcare professionals, physicians, hospitals, pharmacies, and the like. The support network 210 includes the patient's friends, family, as well as others involved in the patient's care. The patient 230, support network 210, and/or the healthcare system 205 may provide reference information 215 to the control system 220. The reference information 215 is used to setup or configure the control system 220. By way of a non-limiting example, the reference information 215 may include patient information (e.g., age, height, weight), patient diagnosis, message routing information, and trigger values. The reference information 215 may also include instructions (e.g., patient instructions) associated with the trigger values. Such instructions may include a predetermined prescribed treatment plan (e.g., instructions to increase a dosage of a diuretic or other medication), instructions to perform a stress test, requests for patient symptom information, instructions to contact healthcare professional, and the like. The reference information 215 may have been provided to a website 217 generated by an optional web server 318 (illustrated in FIG. 3) and forwarded to the control system 220 by the web server 318.

The control system 220 may issue messages 225 to the patient 230 that could cause a modification in the patient's state 235 (e.g., reduce edema or likelihood of edema). When triggered by trigger values, the messages 225 may include one or more instructions associated with the trigger values.

The device 10 is configured to be worn on the patient's limb 11 continuously or occasionally for periods of time. When worn in this manner, the device 10 occasionally (e.g., periodically) collects data that may be processed by the control system 220 to obtain a distance measurement around the patient's limb 11. The distance measurement is referred to herein as a "circumference measurement," independently of whether the portion of the limb whereat the measurement was taken has a substantially circular cross-sectional shape.

The data collected by the device 10 is sent to the control system 220 in a device message 240. The control system 220 analyzes the data received from the device 10 to determine a circumference measurement for the limb 11. Over time, multiple circumference measurements may be collected and tracked for the purposes of detecting a trend or sudden change in the circumference of the limb 11. The previously obtained (or historical) circumference measurements may be stored in the reference information 215.

A healthcare provider or system 205 may access the control system 220 to review the circumference measurement(s) to detect potential problems and/or recommend treatments or changes in treatment. Further, when the control system detects a trend or sudden change in the circumference of the limb 11, the control system 220 may send messages to the healthcare system 205, the support network 210, the patient 230, and the like. When triggered by trigger values, messages sent to the healthcare system 205, the support network 210, the patient 230, and the like may include one or more instructions associated with the trigger values.

Messages sent to the healthcare system 205, the support network 210, and/or the patient 230 may include SMS cellular telephone messages, recorded voice messages (e.g., including educational information), alerts, alarms, and the like.

Thus, the system 200 provides a means of assessing changes in the size of the patient's limb 11, and more particularly the onset of or changes in peripheral edema. The assessment may be conducted remotely by the control system 220 and/or the healthcare system 205. Members of a support network 210 and/or the healthcare system 205 need not be present to collect or evaluate the circumference measurement. Instead, circumference measurements may be collected automatically by the device 10 and optionally, transferred to the system 200. Circumference measurements may be collected on an ongoing basis over any desired length of time.

While peripheral edema is often most pronounced in the lower leg, interstitial swelling is also generally present to a lesser degree in other parts of the body. Therefore, peripheral edema may be measured in other parts of the body. For ease of illustration, the device 10 is described below and illustrated as being worn on a lower portion of a patient's leg near the ankle. However, the device 10 may also be worn on a different portion of a patient's leg (e.g., near the knee, thigh, and the like), a portion of a patient's arm (e.g., on or near the wrist, on the forearm, above the elbow, and the like), a portion of a patient's foot (e.g., on a toe), a portion of a patient's hand (e.g., on a finger), and the like. In other words, the device 10 is not limited to being worn on any particular portion of the body.

Figure 2:
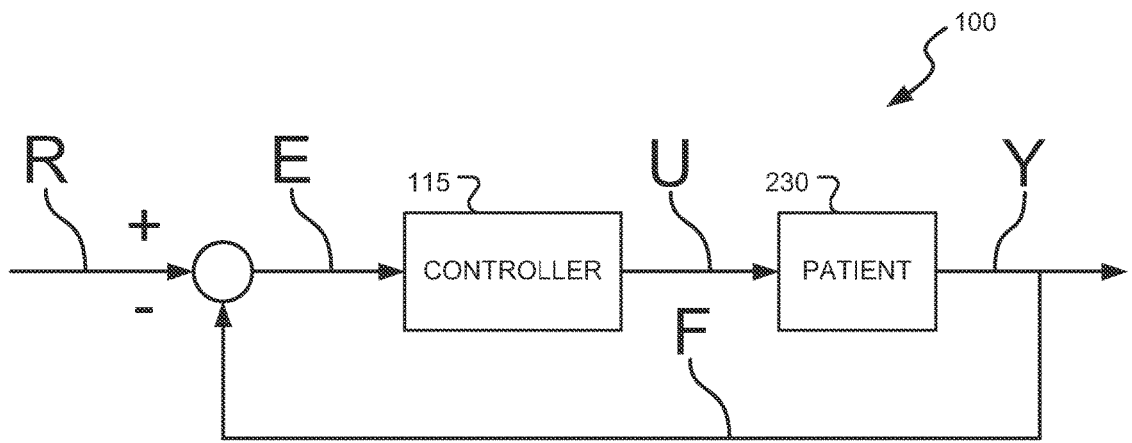
FIG. 2 is a diagram of a control loop implemented by the system of FIG. 1.

The system 200 may be conceptualized as a continually readjusting system that seeks a stable desired condition (e.g., an absence of edema). The system 200 may implement a control loop 100 illustrated in FIG. 2. In the control loop 100, reference information "R" is provided and compared with feedback information "F." With respect to the system 200, the reference information "R" may be the reference information 215 provided to the control system 220, and the feedback information "F" may be the device messages 240 transmitted by the device 10.

The difference between the reference information "R" and the feedback information "F" is an error "E." The error "E" is input into a controller 115. In system 200, the error "E" is calculated by the control system 220. The controller 115 in turn issues commands "U" (e.g., the messages 225) that are used to affect the state of the patient 230. In the system 200, the control system 220 may issue messages 225 to the patient 230, the support network 210, and/or the healthcare system 205. This is reflected in a current state "Y." In FIG. 1, the patient's current state is labeled with reference numeral 235. The current state "Y" provides the feedback information "F" that is compared to the reference information "R." In other words, the patient's state 235 provides the device messages 240 (with data used to obtain the circumference measurement) that are compared to the reference information 215 (e.g., previously obtained circumference measurements). Based on the results of this comparison, one or more messages 225 may be sent to the patient 230, the support network 210, and/or the healthcare system 205 to modify the patient's state 235.

System 300

Figure 3:
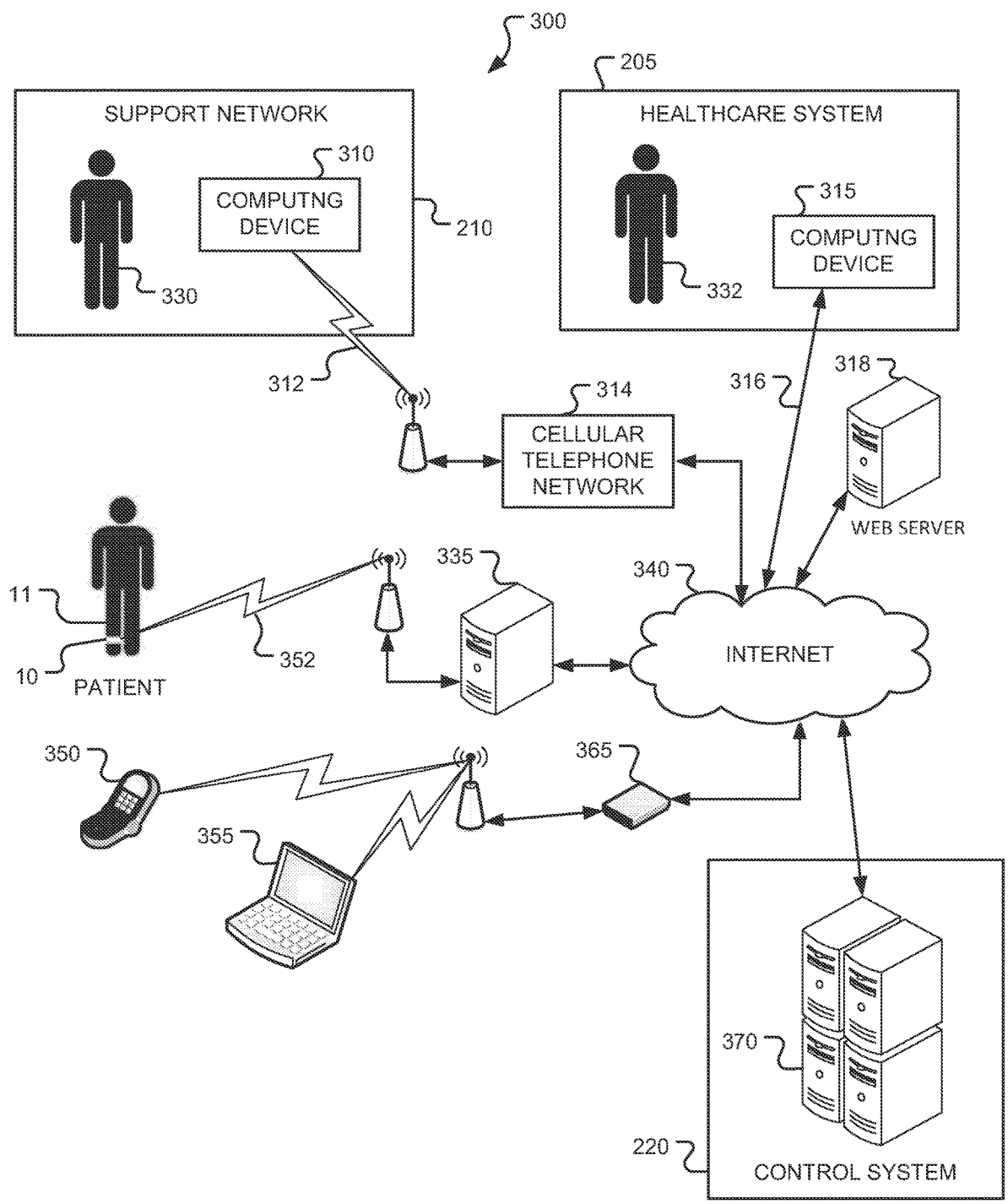
FIG. 3 is a diagram of an embodiment of the system of FIG. 1.

FIG. 3 illustrates a system 300, which is an exemplary implementation of the system 200 (see FIG. 1). Turning to FIG. 3, the control system 220 includes a database server 370. The reference information 215 (see FIG. 1) is stored in a database server 370. The reference information 215 may be received by the database server 370 during an initial setup process as well as on an ongoing basis. The system 300 may include the optional web server 318 configured to generate the website 217 (see FIG. 1) to which the reference information 215 may be provided and transferred to the database server 370 (e.g., over the Internet 340 or other network). The database server 370 may also store pertinent data about the patient 230 (such as patient history, a patient record, and the like), trigger event levels (discussed below), and addresses to which messages (e.g., notifications, alerts, and the like) are to be sent.

Feedback information (e.g., the device message 240 illustrated in FIG. 1) most often originates from the patient 230 and/or the device 10. This feedback information can travel several alternate paths depending upon the implementation details. For example, the feedback information may be input into a computing device (e.g., a patient desktop computer 335, a patient cellular telephone 350, a patient portable computer 355, and the like) connected to the database server 370 (or the web server 318) via the Internet 340. The device 10 may communicate with the computing device via a wired or wireless communication link (e.g., a communication link 352). Over a wireless communication link, the device 10 may communicate with the computing device using SMS messages, WIFI protocols, Bluetooth protocols, and the like. The computing device may transfer the feedback information to the database server 370. The device 10 may communicate the device messages 240 to the computing device for transmission thereby to the database server 370.

In the embodiment illustrated, the patient desktop computer 335 is connected to the Internet 340 via a conventional wired connection.

In the embodiment illustrated, the patient cellular telephone 350 and the patient portable computer 355 are connected to the Internet 340 by an Internet gateway device 365 (e.g., a modem). The patient cellular telephone 350 and the patient portable computer 355 may communicate with the Internet gateway device 365 using WIFI protocols, Bluetooth protocols, and the like.

By way of a non-limiting example, the feedback information may be transmitted by the device 10 via a radio link (e.g., the radio link 352) to the patient desktop computer 335, the patient cellular telephone 350, the patient portable computer 355, and the like. By way of another non-limiting example, the feedback information may be transmitted by the device 10 directly to the Internet gateway device 365.

The feedback information is received by the database server 370. In the embodiment illustrated, the database server 370 implements the control system 220 (see FIG. 1) that compares the current state 235 of the patient 230 and the reference information 215 (which may include previously received feedback information).

One or more messages 225 to be reviewed by the patient 230 may be transmitted by the database server 370 to the device 10, the patient desktop computer 335, the patient cellular telephone 350, the patient portable computer 355, and the like. By way of a non-limiting example, such messages may be displayed on the website 217 (see FIG. 2) generated by the web server 318. In such embodiments, the database server 370 is configured to instruct the web server 318 to display messages on the website 217. The patient desktop computer 335, the patient cellular telephone 350, and/or the patient portable computer 355 may connect to the web server 318 over the Internet and display the website 217 using a conventional web browser application.

The support network 210 may include one or more computing devices (e.g., a support computing device 310) connected to the database server 370 via the Internet 340. One or more messages to be reviewed by a support person 330 may be transmitted by the database server 370 to the computing device 310. By way of a non-limiting example, such messages may be displayed on the website 217 (see FIG. 2) generated by the web server 318. In the embodiment illustrated, the computing device 310 is connected to the Internet 340 via a wireless communication link 312 with a cellular telephone network 314. The computing device 310 may connect to the web server 318 over the Internet and display the website 217 using a conventional web browser application. Some patients may rely on help from the support network 210 while others may have no such support.

The healthcare system 205 may include one or more computing devices (e.g., a caregiver computing device 315) connected to the database server 370 via the Internet 340. One or more messages to be reviewed by a caregiver 332 may be transmitted by the database server 370 to the computing device 315. By way of a non-limiting example, such messages may be displayed on the website 217 (see FIG. 2) generated by the web server 318. In the embodiment illustrated, the computing device 315 is connected to the Internet 340 via a wired communication link 316. The computing device 315 may connect to the web server 318 over the Internet and display the website 217 using a conventional web browser application.

A diagram of hardware and an operating environment in conjunction with which implementations of the database server 370, the patient desktop computer 335, the patient cellular telephone 350, the patient portable computer 355, the support computing device 310, the caregiver computing device 315, and the web server 318 may be practiced is provided in FIG. 19 and described below.

Circuit 400

Figure 4:
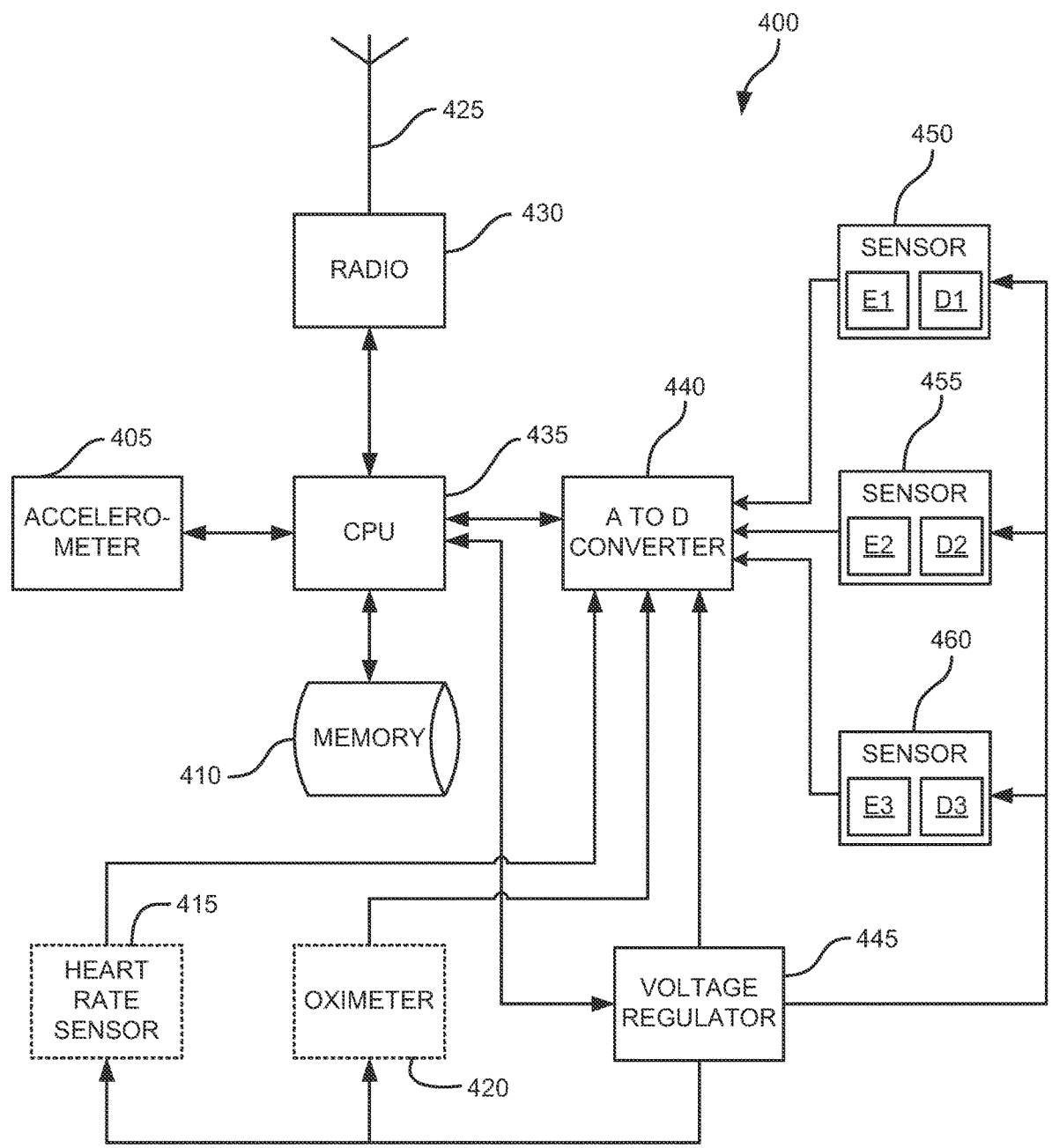
FIG. 4 is a diagram of an exemplary circuit that may be used to construct a device worn on a patient's limb configured to collect patient data used by a control system to determine a circumference of the patient's limb.

FIG. 4 is a block diagram illustrating electrical components of the device 10. The electrical components of the device 10 includes a circuit 400, which includes an accelerometer 405, a memory 410, an antenna 425, a radio 430, a processor 435 (e.g., a CPU), an analog to digital ("A to D") converter 440, a voltage regulator 445, and sensors 450, 455, and 460. Optionally, the circuit 400 may include an oximeter 420 and/or a heart rate sensor 415. Optionally, the circuit 400 may include a capacitive sensor 1530 (see FIG. 15) configured to detect the presence of the limb 11.

The sensors 450, 455, and 460 each emit and detect radiation (e.g., infrared light). The sensor 450 includes an emitter "E1" configured to emit radiation in response to a command received from the processor 435, and a detector "D1" configured to detect radiation of the type emitted by the emitter "E1." The sensor 450 is configured to generate an analog signal indicating how much radiation has been detected by the detector "D1" and transmit the analog signal to the A to D converter 440. The detector "D1" may be configured to detect radiation in response to a command received from the processor 435. The sensor 455 includes an emitter "E2" configured to emit radiation in response to a command received from the processor 435, and a detector "D2" configured to detect radiation of the type emitted by the emitter "E2." The detector "D2" may be configured to detect radiation in response to a command received from the processor 435. The sensor 455 is configured to generate an analog signal indicating how much radiation has been detected by the detector "D2" and transmit the analog signal to the A to D converter 440. The sensor 460 includes an emitter "E3" configured to emit radiation in response to a command received from the processor 435, and a detector "D3" configured to detect radiation of the type emitted by the emitter "E3." The detector "D3" may be configured to detect radiation in response to a command received from the processor 435. The sensor 460 is configured to generate an analog signal indicating how much radiation has been detected by the detector "D3" and transmit the analog signal to the A to D converter 440.

The A to D converter 440 is configured to digitize the analog signals received from the sensors 450, 455, and 460 to produce digital signals. The digital signals are then communicated to the processor 435. The processor 435 may store the digital signals as data in the memory 410 and/or transmit the digital signals via the radio 430 and antenna 425 to an external device (e.g., with reference to FIG. 3, the patient desktop computer 335, the patient cellular telephone 350, the patient portable computer 355, the Internet gateway device 365, and the like). By way of a non-limiting example, the radio 430 may operate at 2.4 GHz and utilize Bluetooth protocol, Bluetooth Low Energy protocol, ZigBee protocol, ANT protocol, and the like. The external device may then transmit the digital signals to the database server 370 (see FIG. 3) via the Internet 340 (see FIG. 3).

The processor 435 may send instructions to the voltage regulator 445 to turn off a section of the circuit 400 including the sensors 450, 455, and 460, the A to D converter 440, the optional oximeter 420, and the optional heart rate sensor 415 to save power. Further, the processor 435 may send instructions to the voltage regulator 445 to turn on the section of the circuit including the sensors 450, 455, and 460, the A to D converter 440, the optional oximeter 420, and the optional heart rate sensor 415.

By way of a non-limiting example, the processor 435 may send instructions to the voltage regulator 445 to turn off the section of the circuit 400 when the capacitive sensor 1530 (see FIG. 15) does not detect the presence of the limb 11. Further, the processor 435 may send instructions to the voltage regulator 445 to turn on the section of the circuit 400 when the capacitive sensor 1530 (see FIG. 15) detects the presence of the limb 11. The capacitive sensor 1530 may be configured to generate an analog signal indicating the presence (or absence) of the limb 11 and transmit the analog signal to the A to D converter 440. The A to D converter 440 is configured to digitize the analog signal received from the capacitive sensor 1530 to produce a digital signal that is communicated to the processor 435. The processor 435 analyzes the digital signal and determines whether the capacitive sensor 1530 detected the presence of the limb 11.

The circuit 400 may be connected to a battery 1620 (see FIG. 17) and powered thereby. Error can be introduced by drift in battery voltage over time. This issue may be addressed by the voltage regulator 445, which may be configured to provide a substantially stable voltage to the emitters "E1," "E2," and "E3" and detectors "D1," "D2," and "D3." Further, the regulated voltage provided by the voltage regulator 445 may be used by the A to D converter 440 as a reference voltage to gage and scale the voltages received from the detectors "D1," "D2," and "D3" when converting the voltages from analog signals to digital signals.

While in the embodiment illustrated, the circuit 400 is powered by a battery 1620, another portable power source may used, such as a fuel cell, storage capacitor, energy harvested from the patient 230, energy harvested from the environment, and the like.

The accelerometer 405 may be implemented as a three-axis accelerometer configured to detect a direction of the acceleration of gravity (or gravitation force). The accelerometer 405 generates a digital signal encoding this information and communicates the signal to the processor 435. The processor 435 may store the digital signal as device orientation data in the memory 410 and/or transmit the digital signal (or the stored device orientation data) via the radio 430 and antenna 425 to an external device (e.g., with reference to FIG. 3, the patient desktop computer 335, the patient cellular telephone 350, the patient portable computer 355, the Internet gateway device 365, and the like). The external device may transmit the digital signal (or the device orientation data) to the database server 370 (see FIG. 3) via the Internet 340 (see FIG. 3). In embodiments in which the device orientation data is stored in the memory 410, the device orientation data may be deleted from the memory 410 after the device orientation data is transmitted to the database server 370.

The accelerometer 405 may also detect patient motion, which may be used by the control system 220 (see FIG. 2) to determine a level of activity of the patient 230. The accelerometer 405 generates a digital signal encoding patient motion information and communicates the signal to the processor 435. The processor 435 may store the digital signal as patient motion information (e.g., in an activity log) in the memory 410 and/or transmit the digital signal (or the stored patient motion information) via the radio 430 and antenna 425 to an external device (e.g., with reference to FIG. 3, the patient desktop computer 335, the patient cellular telephone 350, the patient portable computer 355, the Internet gateway device 365, and the like). The external device may transmit the digital signal (or the patient motion information) to the database server 370 (see FIG. 3) via the Internet 340 (see FIG. 3). In embodiments in which the patient motion information is stored in the memory 410, the patient motion information may be deleted from the memory 410 after the patient motion information is transmitted to the database server 370.

The optional heart rate sensor 415 senses the heart rate of the patient 230 and generates an analog heart rate signal encoding this information. The analog heart rate signal is transmitted to the A to D converter 440, which converts the analog heart rate signal to a digital heart rate signal and transmits the digital heart rate signal to the processor 435. The processor 435 may store the digital signal as heart rate information in the memory 410 and/or transmit the digital signal (or the stored heart rate information) via the radio 430 and antenna 425 to an external device (e.g., with reference to FIG. 3, the patient desktop computer 335, the patient cellular telephone 350, the patient portable computer 355, the Internet gateway device 365, and the like). The external device may transmit the digital signal (or the heart rate information) to the database server 370 (see FIG. 3) via the Internet 340 (see FIG. 3). In embodiments in which the heart rate information is stored in the memory 410, the heart rate information may be deleted from the memory 410 after the heart rate information is transmitted to the database server 370.

The optional oximeter 420 may be implemented as a SpO2 emitter detector circuit. The optional oximeter 420 senses the blood oxygen of the patient 230 and generates an analog blood oxygen signal encoding this information. The analog blood oxygen signal is transmitted to the A to D converter, which converts the analog blood oxygen signal to a digital blood oxygen signal and transmits the digital blood oxygen signal to the processor 435. The processor 435 may store the digital signal as oxygen information in the memory 410 and/or transmit the digital signal (or the stored oxygen information) via the radio 430 and antenna 425 to an external device (e.g., with reference to FIG. 3, the patient desktop computer 335, the patient cellular telephone 350, the patient portable computer 355, the Internet gateway device 365, and the like). The external device may transmit the digital signal (or the oxygen information) to the database server 370 (see FIG. 3) via the Internet 340 (see FIG. 3). In embodiments in which the oxygen information is stored in the memory 410, the oxygen information may be deleted from the memory 410 after the oxygen information is transmitted to the database server 370.

The capacitive sensor 1530 (see FIG. 15) senses whether the limb 11 is present and generates an analog or digital signal encoding this information. The signal is transmitted to the processor 435 (optionally via the A to D converter for conversion from an analog signal to a digital signal, if necessary). The processor 435 is configured to place the device 10 in a sleep mode if the signal indicates the limb 11 is not present and to maintain the device 10 in the sleep mode until the signal indicates the limb 11 is detected.

Methods

Figure 5:
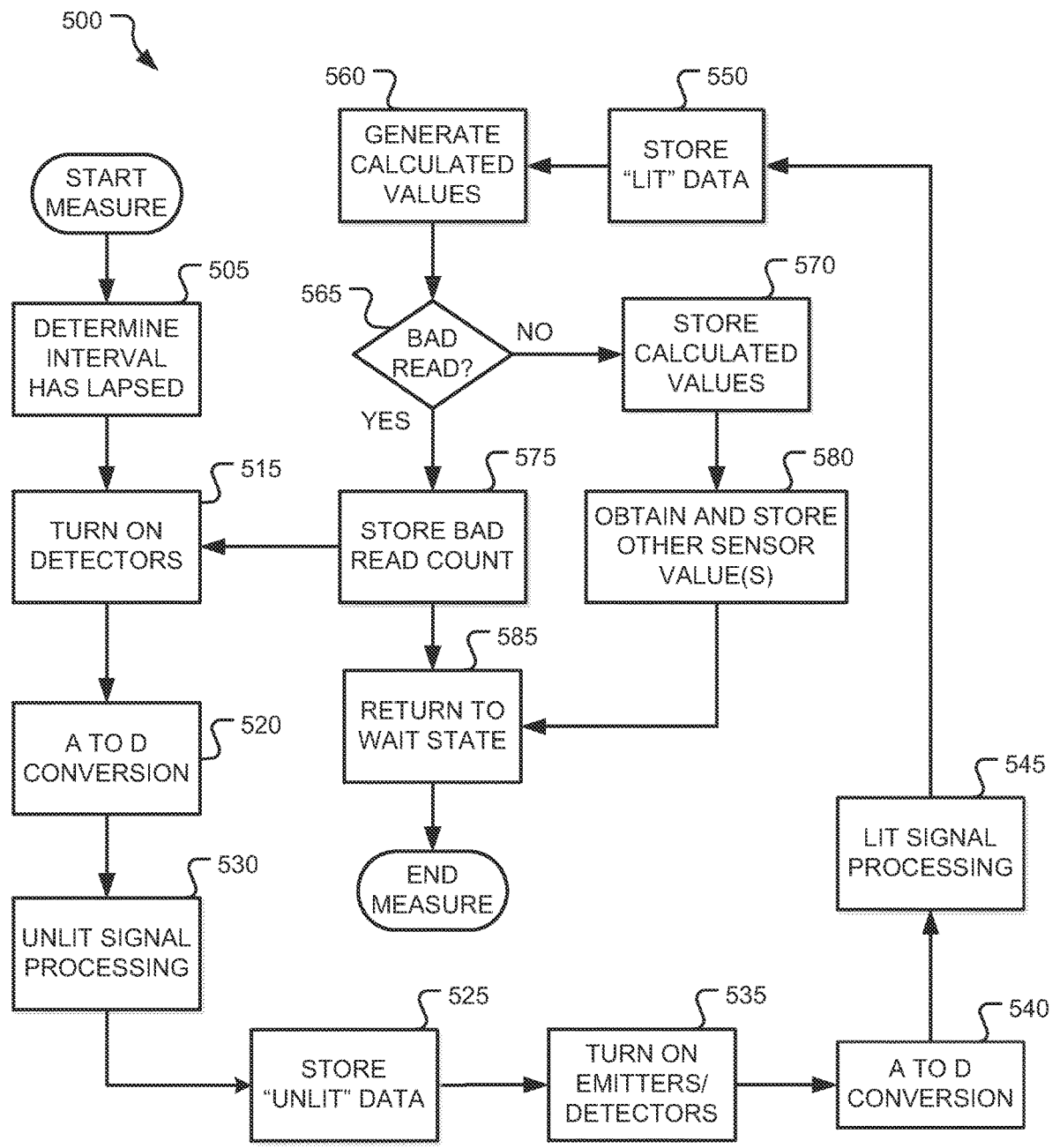
FIG. 5 is a flow diagram of a method of collecting patient data performed the device worn on a patient's limb.

FIG. 5 is a flow diagram of a method 500 performed by the processor 435. The method collects data using the sensor 450, 455, and 460 that is subsequently used by the control system 220 to obtain a circumference measurement. When the method 500 begins, the processor 435 is in a wait state.

In block 505, the processor 435 determines a predetermined measurement interval has lapsed since data was last collected by the device 10. At this point, the processor 435 may turn on the voltage regulator 440 to allow it to stabilize. As mentioned above, the voltage regulator 440 may be used to power the detectors "D1," "D2," and "D3" and the emitters "E1," "E2," and "E3." The voltage regulator 440 may also power the optional oximeter 420 and/or the optional heart rate sensor 415. Thus, turning on the voltage regulator 440 may also turn on the optional oximeter 420 and/or the optional heart rate sensor 415.

Then, in block 515, the processor 435 turns on the detectors "D1," "D2," and "D3" of the sensors 450, 455, and 460, respectively, while, the emitters "E1," "E2," and "E3" remain unlit (i.e., not emitting radiation). The detectors "D1," "D2," and "D3" each sense an amount of radiation and generate an "unlit" analog signal indicating the amount of radiation detected when the emitters "E1," "E2," and "E3" are unlit. Thus, an amount of ambient or background radiation may be detected and used to correct subsequent measurements.

In block 520, the A to D converter 440 receives the "unlit" analog signals from the detectors "D1," "D2," and "D3," digitizes the "unlit" analog signals to produce "unlit" digital signals, and transmits the "unlit" digital signals to the processor 435 for processing.

In block 530, the processor 435 processes the "unlit" digital signals. As is apparent to those of ordinary skill in the art, variation in emitter efficiency and detector sensitivity caused by manufacturing tolerances and position variation may be addressed by calibrating the circuit 400 (see FIG. 4). For example, the circuit 400 may be calibrated initially against a gold standard reflective surface and differences between the voltages received from the detectors "D1," "D2," and "D3" of the sensors 450, 455, and 460 stored and used as calibration data. In block 530, the processor 435 may adjust the "unlit" digital signals using the calibration data. For example, the calibration data may be subtracted from the "unlit" digital signals to equalize the differential efficiencies of emitter/detector pairs of the sensors 450, 455, and 460.

In block 525, the processor 400 may store the "unlit" digital signals and/or the processed "unlit" digital signals in the memory 410 as "unlit" data.

Then, in block 535, the processor 435 turns on both the emitters "E1," "E2," and "E3" and the detectors "D1," "D2," and "D3" simultaneously.

The detectors "D1," "D2," and "D3" each sense an amount of radiation and generate a "lit" analog signal indicating the amount of radiation detected when the emitters "E1," "E2," and "E3" are lit.

In block 540, the A to D converter 540 receives the "lit" analog signals from the detectors "D1," "D2," and "D3," digitizes the "lit" analog signals to produce "lit" digital signals, and transmits the "lit" digital signals to the processor 435 for processing.

In block 545, the processor 435 processes the "lit" digital signals. In block 530, the processor 435 may adjust the "lit" digital signals using the calibration data. For example, the calibration data may be subtracted from the "lit" digital signals to equalize the differential efficiencies of emitter/detector pairs of the sensors 450, 455, and 460.

In block 550, the processor 435 stores the "lit" digital signals and/or the processed "lit" digital signals in the memory 410 as "lit" data.

In block 555, the processor 435 generates calculated values for each of the "lit" digital signals. The calculated values may be determined by subtracting the "unlit" digital signals from the "lit" digital signals. Thus, the calculated values reflect an amount of radiation emitted by the emitters "E1," "E2," and "E3" and subsequently detected by the detectors "D1," "D2," and "D3." Further, the calculated values include a value for each of the sensors 450, 455, and 460.

In decision block 565, the processor 435 evaluates read quality. Read quality may be determined by comparing the calculated values obtained from the detectors "D1" and "D3" with a predetermined "normal" range. If the calculated values are outside the predetermined "normal" range, the processor 435 determines a bad read has occurred. Otherwise, if the calculated values are inside the predetermined "normal" range, the processor 435 determines a good read has occurred.

Optionally, in decision block 565, the calculated values obtained from the detectors "D1" and "D3" may be compared to one another to determine whether the values differ from one another by less than a predetermined minimum amount or more than a predetermined maximum amount. If the calculated values differ from one another by less than the predetermined minimum amount or more than the predetermined maximum amount, the processor 435 determines a bad read has occurred. Otherwise, if the calculated values differ from one another by at least the predetermined minimum amount and no more than the predetermined maximum amount, the processor 435 determines a good read has occurred.

As will be explained below, when the device 10 is properly positioned on the limb 11 of the patient 230, the calculated value for the detector "D2" is within a predetermined range because the detector "D2" is adjacent a solid portion "GS" (see FIG. 9) of an optical gradient 1545 (see FIG. 9) having a substantially constant reflectivity. If the calculated value for the detector "D2" is not within the predetermined range, the processor 435 determines a bad read has occurred. On the other hand, if the calculated value for the detector "D2" is within the predetermined range, the processor 435 determines a good read has occurred.

The decision in decision block 565 is "YES," when a "bad" read has occurred. On the other hand, the decision in decision block 565 is "NO," when an acceptable read has occurred.

When the decision in decision block 565 is "NO," in block 570, the processor 435 stores the calculated values in the memory 410.

In block 580, the processor 435 obtains one or more accelerometer values from the accelerometer 405 and stores the accelerometer value(s) in the memory 410. The accelerometer value(s) may include an activity log that includes information about patient activity levels. In block 580, the processor 435 may also obtain data from the oximeter 420 and/or the heart rate sensor 415 and store that data in the memory 410.

Then, in block 585, the processor 435 returns to the wait state and the method 500 terminates.

When the decision in decision block 565 is "YES," in block 575, the processor 435 stores a bad read count in the memory 410 and returns to block 515. In block 575, the processor 435 may also evaluate the number of bad reads stored and set an error flag, if required.

Then, in block 585, the processor 435 returns to the wait state and the method 500 terminates.

FIG. 6A is a flow diagram of a method 600 of transferring data from the device 10 to the control system 220.

When the method 600 begins, the processor 435 is in the wait state. In block 605, the processor 435 determines a predetermined transmission interval has lapsed since a transmission was last sent by the device 10 to an external device (e.g., e.g., the patient desktop computer 335, the patient cellular telephone 350, the patient portable computer 355, the Internet gateway device 365, and the like). As discussed above, the external device is configured to transfer the data sent to it by the device 10 to the control system 220.

In block 615, the processor 435 retrieves the calculated values, the accelerometer value(s), and optionally the data obtained from the oximeter 420 and/or the heart rate sensor 415 stored in the memory 410 (see FIG. 4) in blocks 570 and 580 of the method 500 (see FIG. 5). In block 620, the information retrieved is formatted for transmission (e.g., placed in transmission packets) and subsequently transferred to the external device in block 630.

In decision block 635, the processor 435 determines whether a transfer confirmation has been received from the external device. The decision in decision block 635 is "YES" when the device 10 has received a transfer confirmation from the external device in response to the transmission sent in block 630. Otherwise, the decision in decision block 635 is "NO" when the device 10 has not received a transfer confirmation from the external device in response to the transmission sent in block 630. Optionally, even if a transfer confirmation is received, the decision in decision block 635 may nevertheless be "NO," if the processor 435 determines that a problem occurred when the calculated values were transmitted in block 630.

When the decision in decision block 635 is "YES," the method 600 terminates.

When the decision in decision block 635 is "NO," in block 640, the processor 435 stores bad send data in the memory 410 for analysis. Then, the processor 435 returns to block 615.

FIG. 6B is a flow diagram of a method 650 performed by the processor 435. The method 650 is performed when the device 10 receives data from the control system 220. The device 10 may receive data from the control system 220 following the successful transfer of data (e.g., the calculated values, the accelerometer value(s), and optionally the data obtained from the oximeter 420 and/or the heart rate sensor 415) to the control system 220.

In first block 652, the processor 435 waits to receive a transmission from the control system 220.

In block 655, the device 10 receives data, such as a setting value, constant value, and the like, from the control system 220.

In block 660, the processor 435 determines whether a problem occurred when the data was received from the control system 220. For example, if too much time has elapsed since data was last received from the control system 220, the processor 435 may determine a problem occurred. The decision in decision block 660 is "YES," when the processor 435 determines a problem has occurred. On the other hand, the decision in decision block 660 is "NO," when the processor 435 determines a problem has not occurred.

When the decision in decision block 660 is "YES," in block 665, the processor 435 stores data related to the problem (e.g., increments a bad receive count value). Then, the processor 435 returns to block 652 to wait for additional transmissions from the control system 220. By way of an example, the control system 220 may retransmit data to the device 10 if the control system 220 determines the data was not received by the device.

When the decision in decision block 660 is "NO," in optional block 670, the processor 435 may send a receipt confirmation to the control system 220 confirming the data was received. Then, in block 680, the device 10 stores the data received and the method 650 terminates.

Figure 7:
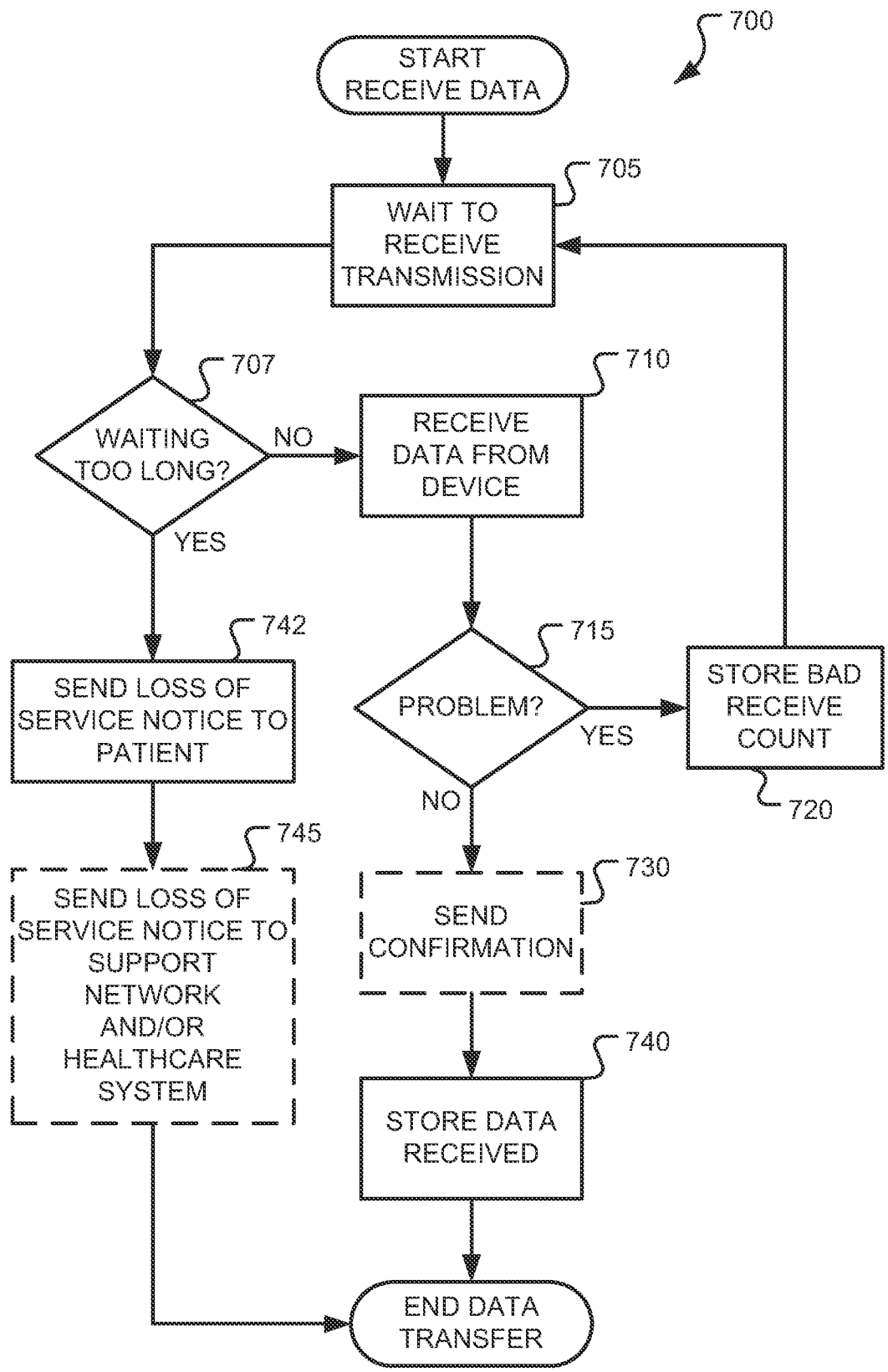
FIG. 7 is a flow diagram of a method performed by the control system when receiving the patient data from the device worn on a patient's limb.

FIG. 7 is a flow diagram of a method 700 of receiving the calculated values at the control system 200. By way of a non-limiting example, the method 700 will be described as being performed by the database server 370 (see FIG. 3).

In first block 705, the database server 370 waits to receive a transmission from the device 10 (via one of the external devices). In decision block 707, the database server 370 determines whether it has been waiting too long (e.g., longer than a predetermined amount of time) indicating there may be a problem with the device 10 or, in embodiments of the device 10 configured to communicate wirelessly, that the device 10 was positioned outside a radio coverage area. The decision in decision block 707 is "YES" when the database server 370 has been waiting too long for a transmission from the device 10. On the other hand, the decision in decision block 707 is "NO" when the database server 370 has not been waiting too long for a transmission from the device 10.

When the decision in decision block 707 is "NO," the database server 370 continues to wait and in block 710, receives the transmission (including the calculated values, accelerometer value(s), and optionally the data obtained from the oximeter 420 and/or the heart rate sensor 415) from the device 10.

In decision block 715, the database server 370 determines whether a problem occurred when the calculated values, accelerometer value(s), and optionally the data obtained from the oximeter 420 and/or the heart rate sensor 415 were received from the device 10. For example, the calculated value for the detector "D1" may be compared to a valid range stored in the database server 370. If the calculated value for the detector "D1" is outside the valid range, the database server 370 may determine a problem occurred. The decision in decision block 715 is "YES," when the database server 370 determines a problem has occurred. On the other hand, the decision in decision block 715 is "NO," when the database server 370 determines a problem has not occurred.

When the decision in decision block 715 is "YES," in block 720, the database server 370 stores data related to the problem (e.g., increments a bad receive count value). Then, the database server 370 returns to block 705 to wait for additional transmissions from the device 10. By way of an example, the device 10 may retransmit data to the control system 220 if the device 10 determines the formatted data was not received by the control system.

When the decision in decision block 715 is "NO," in optional block 730, the database server 370 may send a receipt confirmation to the device 10 confirming the calculated values, accelerometer value(s), and optionally the data obtained from the oximeter 420 and/or the heart rate sensor 415 were received. In block 740, the database server 370 stores the calculated values, accelerometer value(s), and optionally the data obtained from the oximeter 420 and/or the heart rate sensor 415 received. Then, the method 700 terminates. The calculated values, accelerometer value(s), and optionally the data obtained from the oximeter 420 and/or the heart rate sensor 415 may be stored in a patient record associated with the device 10. By way of a non-limiting example, the transmission received by the control system 220 may include a device identifier associated with the device 10 that may be used to identify the patient record associated with the device.

When the decision in decision block 707 is "YES," the database server 370 has been waiting too long for a transmission from the device 10 and in block 742, sends a notification indicating a problem has occurred to the device 10, the patient desktop computer 335, the patient cellular telephone 350, and/or the patient portable computer 355 to be reviewed by the patient 230. In optional block 745, the database server 370 may send a notification to the support network 210 and/or the healthcare system 205 indicating a problem has occurred. Then, the method 700 terminates.

Figure 13:
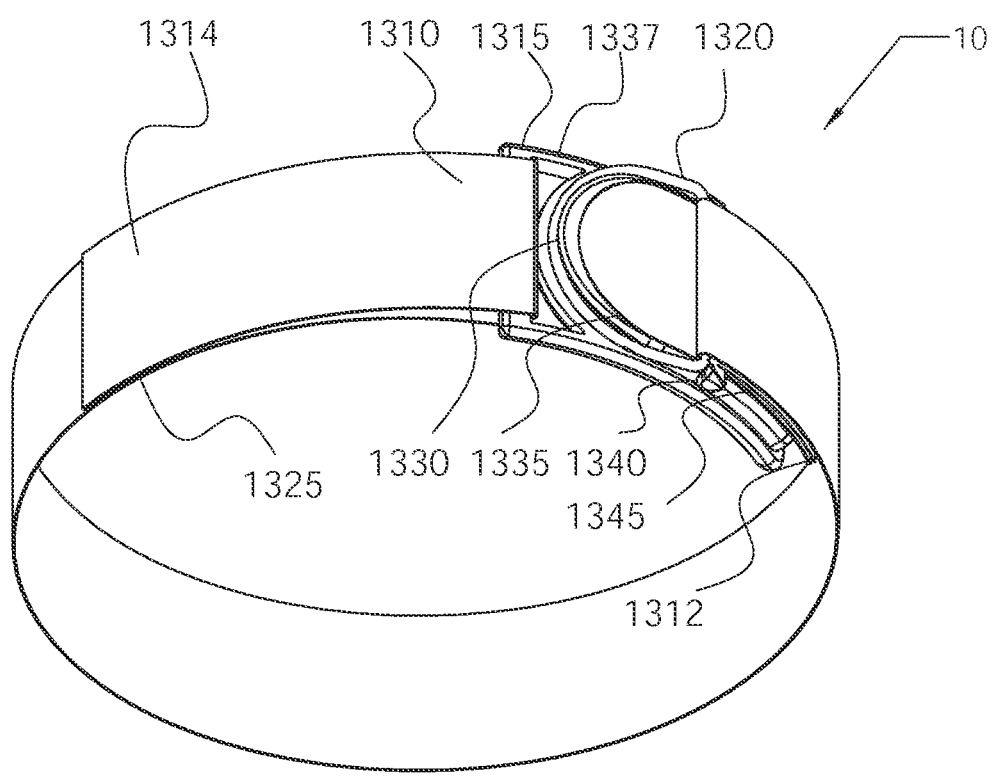
FIG. 13 is a perspective view of an embodiment of the device worn on a patient's limb.
Figure 14:
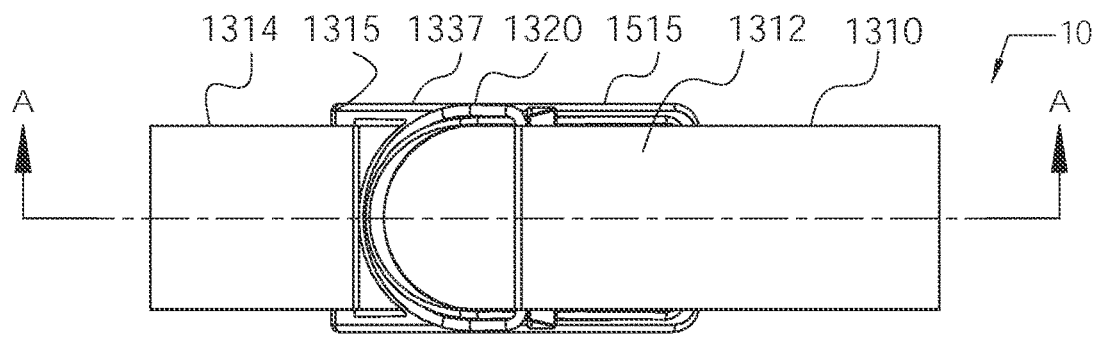
FIG. 14 is front view of the device of FIG. 13.
Figure 17:
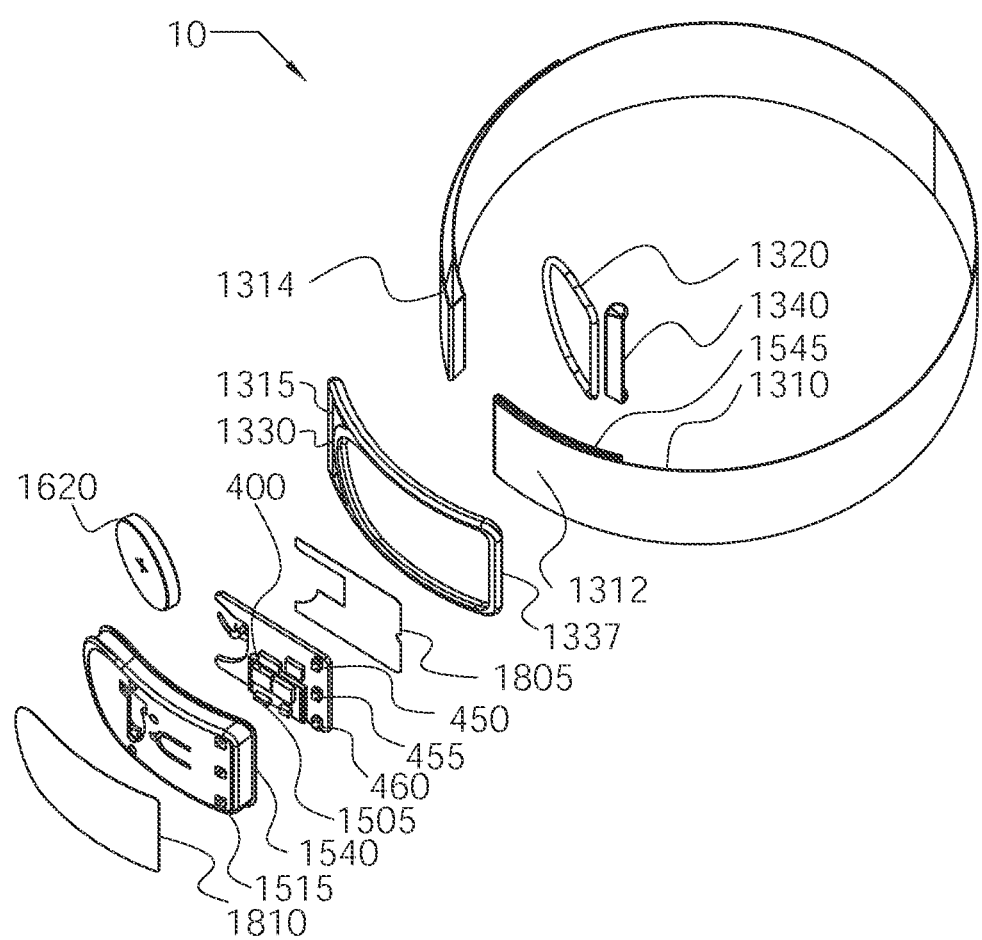
FIG. 17 is an exploded perspective view of the device of FIG. 13.
Figure 18:
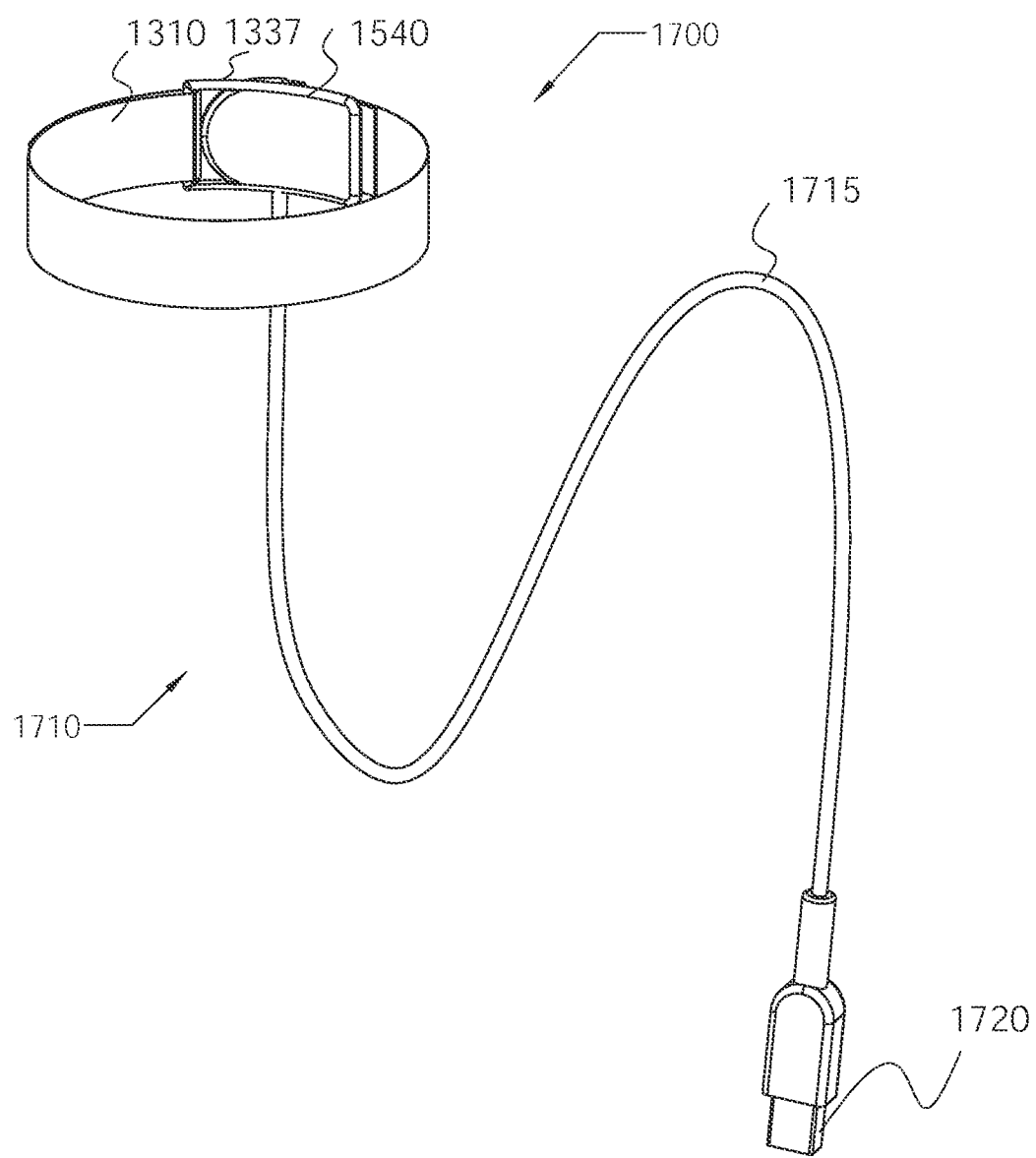
FIG. 18 is a perspective view of an alternate embodiment of the device of FIG. 13.

Referring to FIGS. 13 and 17, as will be explained in greater detail below, the device 10 includes a flexible but inelastic strap 1310 having a first end portion 1312 opposite a second end portion 1314. An optical gradient 1545 is coupled to the first end portion 1312. An electronics enclosure 1335 is coupled to the second end portion 1314 by a guide portion 1315 of a frame member 1337 positioned about the periphery of the electronics enclosure 1335.

The electronics enclosure 1335 includes a sensor portion 1515. The emitter "E1" and detector "D1" of the sensor 450, the emitter "E2" and detector "D2" of the sensor 455, and the emitter "E3" and detector "D3" of the sensor 460 are positioned on the sensor portion 1515 of the electronics enclosure 1335.

The first end portion 1312 is coupled to the electronics enclosure 1335 by a tensioning member 1320. When the first end portion 1312 is coupled to the electronics enclosure 1335, the sensor portion 1515 extends under the first end portion 1312 of the strap 1310 and the emitters "E1," "E2," and "E3" and detectors "D1," "D2," and "D3" face toward the optical gradient 1545 coupled to the first end portion 1312 of the strap 1310.

Figure 10A:
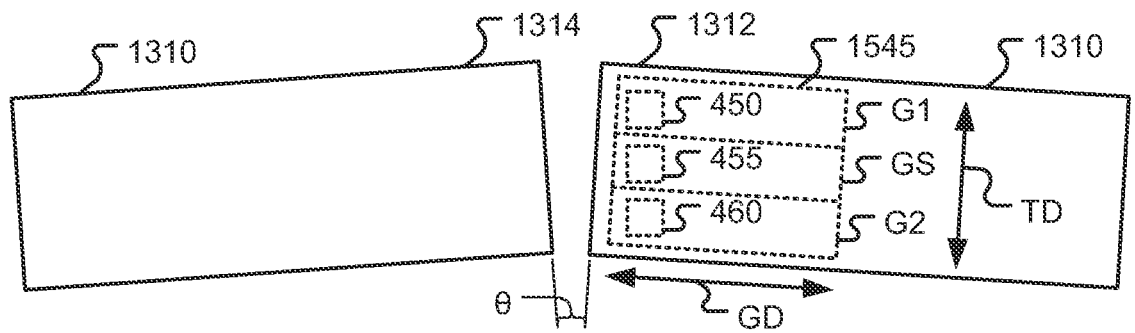
FIG. 10A is an illustration the device positioned on the patient's limb at a location above a minimum circumference of the patient's limb depicting a strap, optical gradient, and sensors that may be used to construct the device.
Figure 10B:
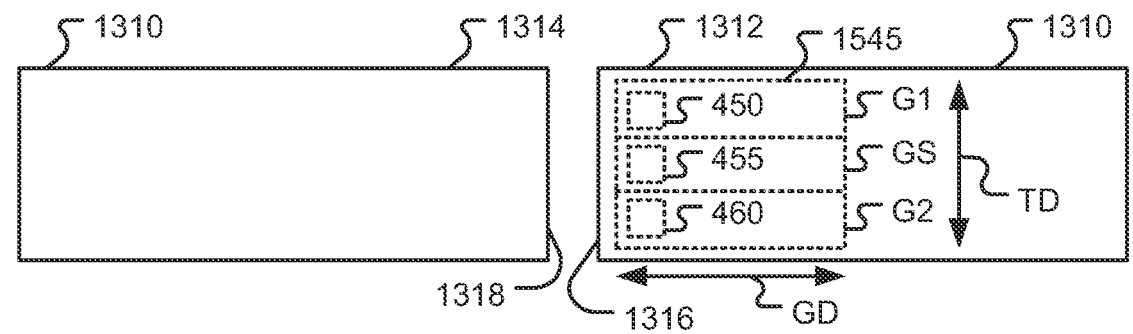
FIG. 10B is an illustration the device positioned on the patient's limb at the location of the minimum circumference of the patient's limb depicting the strap, optical gradient, and sensors that may be used to construct the device.

The tensioning member 1320 is elastic and may be stretched to accommodate the patient's limb 11. Referring to FIG. 10B, when the strap 1310 is wrapped snuggly around a cylinder, edges 1316 and 1318 the first and second end portions 1312 and 1314, respectively, will be substantially parallel with one another. However, when the strap 1310 is wrapped snuggly about a tapered object (e.g., a wrist, an ankle, and the like), the strap 1310 will follow the tapered surface of the object and the edges 1316 and 1318 the first and second end portions 1312 and 1314, respectively, will not be substantially parallel with one another. In other words, an angle "θ" is defined between the edges 1316 and 1318 when the strap 1310 is wrapped snuggly about a tapered object (e.g., a wrist, an ankle, and the like).

Figure 9:
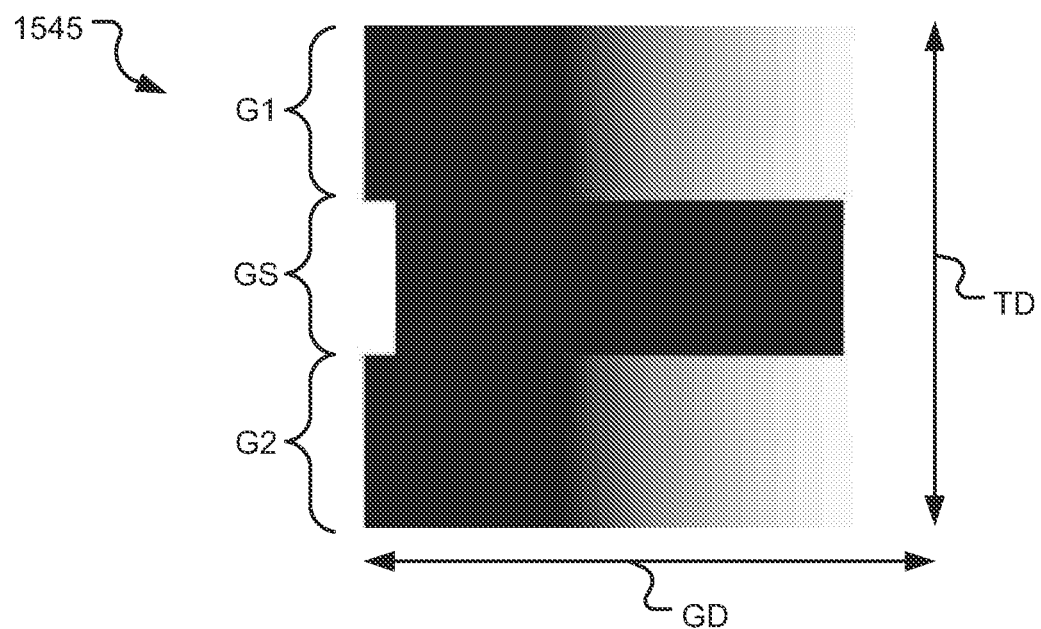
FIG. 9 is an illustration of an exemplary optical gradient that may be used to construct the device worn on a patient's limb.

As mentioned above, the sensors 450, 455, and 460 are adjacent the optical gradient 1545. The sensors 450, 455, and 460 are positioned such that light emitted by the emitters "E1," "E2," and "E3" is reflected by the optical gradient and detected by the detectors "D1," "D2," and "D3," respectively. Referring to FIG. 9, the exemplary optical gradient 1545 illustrated includes a first gradient portion "G1," a second gradient portion "G2," and a solid portion "GS" positioned between the first and second gradient portions. In the embodiment illustrated, reflectivity of the first and second gradient portions "G1" and "G2" changes linearly along a gradient direction (indicated by an arrow "GD"). However, reflectivity of the solid portion "GS" does not change along the gradient direction (indicated by an arrow "GD"). In the embodiment illustrated, the reflectivity of the first and second gradient portions "G1" and "G2" is greater toward the right hand side than toward the left hand side of FIG. 9. Further, the first and second gradient portions "G1" and "G2" are aligned along a transverse direction (indicated by an arrow "TD") such that along the transverse direction the reflectivity of the first gradient portion "G1" is substantially identical to the reflectivity of the second gradient portion "G2." Thus, for each location along the gradient direction (indicated by an arrow "GD"), the first gradient portion "G1" has a reflectivity substantially identical (or corresponding) to the reflectivity of the second gradient portion "G2."

The sensor 450 is positioned adjacent to the first gradient portion "G1," the sensor 455 is positioned adjacent to the solid portion "GS," and the sensor 460 is positioned adjacent to the second gradient portion "G2." Thus, the calculated value for sensor 455 should not vary based on the positioning of the sensor 455 relative to the solid portion "GS" along the gradient direction (indicated by the arrow "GD"). However, the calculated values for the sensors 450 and 460 will vary based on the positioning of the sensors 450 and 460 relative to the first and second gradient portions "G1" and "G2," respectively, along the gradient direction (indicated by the arrow "GD"). As will be explained in more detail below, the calculated value for the sensor 455 may be used to verify the alignment of the sensors 450, 455, and 460 with the optical gradient 1545, and the calculated values for the sensors 450 and 460 may be used to determine the position of the device 10 on the patient's limb 11 and a circumference measurement of the patient's limb.

Figure 8A:
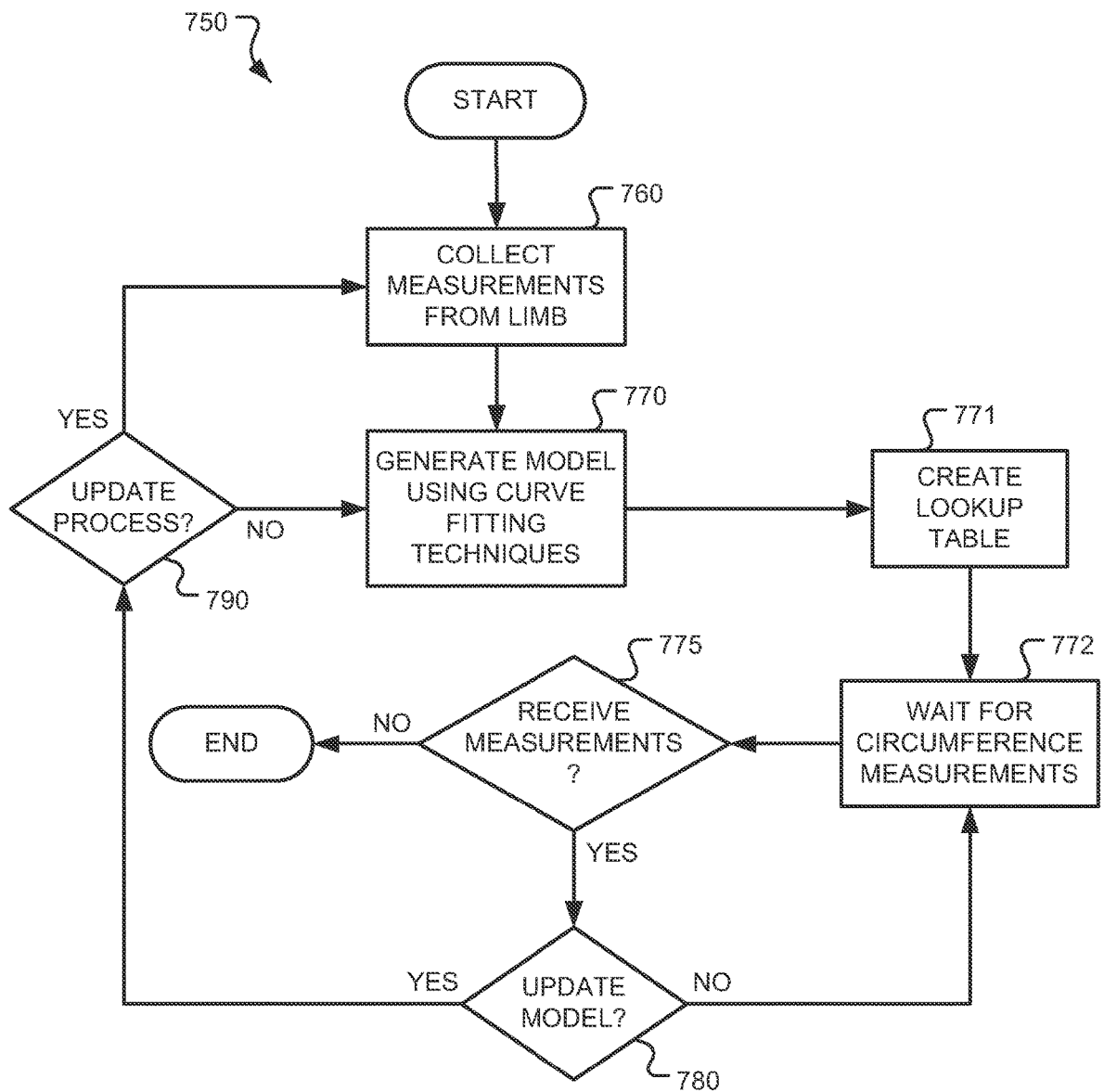
FIG. 8A is a flow diagram of a method of constructing a model of the patient's limb.

FIG. 8A is a flow diagram of a method 750 of creating a model of the patient's limb 11 for use by a method 800 describe below and illustrated in FIG. 8B. The method 750 may be performed by the device 10, the control system 220, and/or a combination thereof. The model correlates positions along the longitudinal axis of the limb 11 with a measure of the distance around the limb 11. The calculated values received by the database server 370 indicate how much radiation was detected by the detectors "D1," "D2," and "D3." As explained above, the amount of radiation detected by the detectors "D1," "D2," and "D3" varies based on where the detectors are positioned relative to the optical gradient 1545 (see FIG. 9). Where the detectors "D1," "D2," and "D3" are positioned relative to the optical gradient 1545 varies with the distance around the patient's limb 11 (or the limb's circumference) in the location on the limb whereat the device 10 is positioned. Therefore, the calculated values may be used as the measure the distance around the patient's limb 11 in the model. In such embodiments, the database server 370 may determine changes in the distance around the patient's limb 11 using the calculated values without actually determining the distance around the patient's limb 11. Alternatively, the calculated values (which measure an amount of radiation) may be used to obtain distance measurements. In such embodiments, the distance measurements obtained from the calculated values may be used as the measure the distance around the patient's limb 11 in the model. By way of a non-limiting example, the calculated values may be converted into distance measurements by correlating the amount of radiation detected with a circumference measurement.

For ease of illustration, the distance measurements (or circumference measurements) obtained from the calculated values will be described as being the measure the distance around the patient's limb 11 used in the model. However, this is not a requirement and embodiments in which a different measure of the circumference of the limb 11 is used to generate the model are also within the scope of the present teachings.

Figure 12:
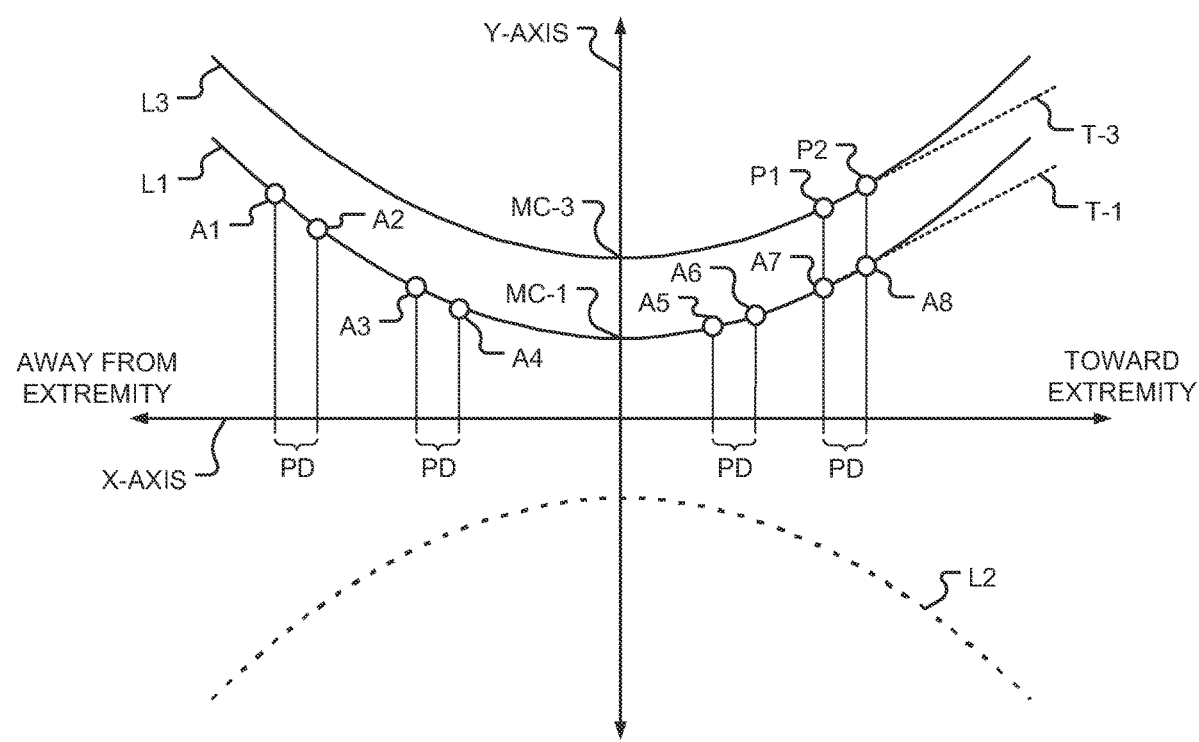
FIG. 12 is a graph illustrating the patient data a model of the patient's limb.

FIG. 12 is a graph in which the x-axis corresponds to the longitudinal axis of the limb 11 and the y-axis corresponds to the distance around the around the patient's limb 11. The limb 11 (see FIG. 1) may be modeled as a three-dimensional surface (e.g. a hyperboloid of one sheet) that is symmetric about a longitudinally axis (e.g., the x-axis). Such a model may be created by rotating a contoured line (e.g., a solid contoured line "L1") spaced apart from and extending along the longitudinally axis about the longitudinally axis. In FIG. 12, a dashed line "L2" illustrates the contoured line "L1" rotated about the x-axis. The area between the contoured line "L1" and the dashed line "L2" represents a cross-sectional area (through the longitudinal axis) of a portion of the limb 11.

The contoured line "L1" models the circumference of the limb 11 at a range of locations along the longitudinal axis of the limb. The contoured line "L1" may be defined by a predefined mathematical equation and one or more circumference measurements (illustrated as points "A1" to "A8") collected from the patient's limb 11. The predefined mathematical equation may be fit to the patient's limb 11 using the one or more circumference measurements (illustrated as points "A1" to "A8") collected from the limb 11. In other words, curve fitting techniques may be used to derive the contoured line "L1" by modifying a mathematical equation based on circumference measurements collected from the limb 11.

In FIG. 12, the contoured line "L1" used to model the patient's limb 11 is a parabola. In FIG. 12, a minimum circumference "MC-1" of the model of the limb 11 is positioned on the y-axis above an intersection of the x-axis and the y-axis. For ease of illustration, in FIG. 12, the right-hand side of the x-axis is extending toward an extremity (e.g., a hand or a foot) and the left-hand side of the x-axis is extending away from the extremity. At the wrist, the arm typically narrows (or has a smaller circumference). Similarly, at the ankle, the leg typically narrows (or has a smaller circumference). Therefore, the minimum circumference "MC-1" may be used as the circumference measurement of the limb 11.

Turning to FIG. 8A, in first block 760, circumference measurements (e.g., those illustrated as points "A1" to "A8") are collected from the patient's limb 11. In block 760, a setup operation may be performed by the patient 230, the support person 330, the caregiver 332, a combination thereof, and the like, in which the device 10 is positioned at different locations along the patient's limb 11. At each location, the device 10 is used to capture at least one circumference measurement. During the setup operation, the device 10 may be positioned in predetermined locations so the control system 220 can readily correlate each of the circumference measurements with a position on the patient's limb 11. The patient 230, the support person 330, and/or the caregiver 332 may inform (e.g., via the website 217) the control system 220 that the setup operation is being performed. Alternatively, the control system 220 may instruct the patient 230, the support person 330, and/or the caregiver 332 to perform the setup operation (e.g., via the website 217).

During the setup operation the method 500 illustrated in FIG. 5 may be used to collect calculated values for each location in which the device 10 is positioned. When collecting calculated values, in block 505, the method 500 uses the predetermined measurement interval. However, during the setup operation, a different interval (e.g., a shorter interval) may be used in block 505. Further, the device 10 may include an indicator (not shown) that may indicate when calculated values have been collected for a particular location so that the person positioning the device on the limb 10 may reposition the device 10 in a next position. The indicator (not shown) may include a speaker, a light, and the like. In such embodiments, the device 10 may produce a sound and/or illuminate a light each time the method 500 terminates during the performance of the setup operation. Alternatively, the device 10 may include a manually operable switch (e.g., a button) that the person positioning the device 10 may activate to indicate the device has been repositioned and the method 500 should be performed by the processor 435 (see FIG. 4).

The method 600 (see FIG. 6) is performed one or more times by the processor 435 (see FIG. 4) to transfer the calculated values obtained during the setup operation to the database server 370 (see FIG. 3). The method 700 (see FIG. 7) is performed one or more times by the database server 370 (see FIG. 3) to receive the calculated values obtained during the setup operation from the processor 435 (see FIG. 4).

After the database server 370 (see FIG. 3) has received the calculated values obtained during the setup operation from the processor 435 (see FIG. 4), in block 770, the database server 370 performs curve fitting techniques to generate a model of the patient's limb 11 based on the circumference measurements obtained from the calculated values. As explained above, the calculated values may be converted or otherwise used to obtain circumference measurements. Further, in some embodiments, the calculated values may be used as the circumference measurements.

Those of ordinary skill in the art appreciate that the device 10 illustrated does not collect a measurement of the position of the device 10 along the limb 11. In other words, the device 10 collects the y-coordinate of the points "A1" to "A8" but not the x-coordinate. As mentioned above, during the setup operation, the device 10 may be positioned in predetermined locations so the control system 220 can readily correlate each of the circumference measurements with a position on the patient's limb 11.

By way of another example, each pair of circumference measurements (collected using the sensors 450 and 460 illustrated in FIG. 4) may be used to determine the position of the device 10 on the patient's limb 11 (e.g. the x-coordinates of the points "A1" to "A8") for the purposes of generating the model. In FIG. 12, the pairs include a first pair of circumference measurements (illustrated as points "A1" and "A2"), a second pair of circumference measurements (illustrated as points "A3" and "A4"), a third pair of circumference measurements (illustrated as points "A5" and "A6"), and a fourth pair of circumference measurements (illustrated as points "A7" and "A8").

The circumference measurements in each of the pairs are spaced apart by a predetermined distance "PD." The predetermined distance "PD" may be substantially equal to a distance (e.g., about 20 millimeters) between the sensor 450 and the sensor 460. When the pairs of circumference measurements are collected, the strap 1310 is allowed to follow the surface of the patient's limb 11 and minor measurement deviations caused by non-planar aspects of the limb 11 may be ignored. Each of the pairs of circumference measurements may be used to determine an amount of taper in the patient's limb 11 between the locations whereat the measurements were taken. By way of an example, a line "T1" illustrates an amount of taper between the circumference measurements (illustrated as points "A7" and "A8") of the fourth pair.

Further, if the orientation of the device 10 is known, the direction of the taper may be used to determine whether a pair of circumference measurements is positioned at or near the minimum circumference "MC-1," toward the extremity relative to the minimum circumference "MC-1," or away from the extremity relative to the minimum circumference "MC-1."

The orientation of the device 10 may be determined by performing orientation signal processing on the accelerometer value(s) transferred with the calculated values. By way of a non-limiting example, an accelerometer with three orthogonal sensing elements detects static deflections in each of the sensing elements that can be used to determine gravitation direction and thus device orientation. Such orientation signal processing is known in the art and will not be described in detail. If at the time of a measurement, the accelerometer value(s) indicate the device 10 is horizontal (i.e., the acceleration of gravity is substantially orthogonal to the longitudinal axis of the limb 11), a previously determined orientation of the device 10 may be used. For example, the most recently determined non-horizontal orientation may be used.

In alternate embodiments, instead of pairs of circumference measurements spaced apart by the predetermined distance "PD," a single circumference measurement (e.g., the point "A7" in FIG. 12) and the angle "θ" (see FIGS. 10A and 10B) may be used to define the contoured line "L1." The angle "θ" may serve the same purpose as the second circumferential measurement of each of the pairs of circumferential measurements discussed above. Specifically, the angle "θ" may be used to determine an amount of taper in the patient's limb 11 whereat the circumference measurement was taken. Using multiple circumference measurements and angle "θ" for each circumference measurement, the contoured line "L1" (e.g., a parabolic curved line) may be defined using curve fitting techniques.

In block 771, the database server 370 uses the circumference measurements collected during the setup operation and/or an update operation (discussed below) to generate a lookup table (not shown). Returning to FIG. 12, a difference between the circumference measurements of each of the pairs (referred to as a "circumference differential value") may be correlated with a position along the longitudinal axis of the limb 11. For example, the difference between the y-coordinates of the first pair of circumference measurements (plotted as points "A1" and "A2") is larger than the difference between the y-coordinates of the second pair of circumference measurements (plotted as points "A3" and "A4"), indicating the first pair is farther from the minimum circumference "MC-1" than the second pair.

The lookup table may list the following values for each pair of circumference measurements:
1) at least one of the circumference measurements of the pair of circumference measurements;
2) the circumference differential value; and
3) the minimum circumference "MC-1."

As will be explained below, the lookup table may be used by the database server 370 to determine whether the circumference of the limb 11 has changed.

In block 772, the database server 370 waits to receive new circumference measurements from the device 10. By way of a non-limiting example, the database server 370 may wait for a predetermined interval.

In decision block 775, the database server 370 determines whether new circumference measurements have been received. The decision in decision block 775 is "YES" when new circumference measurements have been received. On the other hand, the decision in decision block 775 is "NO" when new circumference measurements have not been received.

When the decision in decision block 775 is "NO," the method 750 terminates.

When the decision in decision block 775 is "YES," in decision block 780, the database server 370 determines whether to update the model. The decision in decision block 780 is "YES" when the database server 370 decides to update the model. On the other hand, the decision in decision block 780 is "NO" when the database server 370 decides not to update the model.

When the decision in decision block 780 is "NO," the database server 370 returns to block 772 to wait for new circumference measurements.

When the decision in decision block 780 is "YES," new circumference measurements are used to update or modify the model. The new circumference measurements may be those accumulated as the device 10 is worn by the patient 230 (e.g., the new circumference measurements received before decision block 775) and/or new circumference measurements collected during an update operation.

Further, other information, such as patient height and weight may be considered and used to modify the model.

For example, if the patient 230 has gained weight other than by the retention of fluids, an increase in limb circumference may merely be the result of the weight gain. Therefore, the model (e.g., equation defining the contoured line "L1") may be updated to reflect the change in limb size.

In decision block 790, the database server 370 determines whether to perform the update operation, which may be substantially similar to the setup operation. The decision in decision block 790 is "YES" when the database server 370 decides to perform the update operation. On the other hand, the decision in decision block 790 is "NO" when the database server 370 decides not to perform the update operation.

The setup or update operations may be performed when the length of the strap 1310 is adjusted (e.g., tightened or loosened). Further, the setup or update operations may be performed when the strap 1310 is replaced because manufacturing variations may exist in the reflective qualities of the optical gradient 1545 or strap 1310. This setup or update operations may be performed by the control system 220 automatically. Further, a user (e.g., the patient 230, the support person 330, the caregiver 332, and the like) may initiate the performance of the setup or update operations (e.g., in response to a recalibration notice).

When the decision in decision block 790 is "YES," the block 760 is performed to collect the new circumference measurements. Then, in block 770, the database server 370 regenerates the model using the circumference measurements collected during the setup operation, the new circumference measurements collected during the update operation, and optionally, the new circumference measurements collected (before decision block 775) as the device 10 was worn by the patient 230.

When the decision in decision block 790 is "NO," in block 770, the database server 370 regenerates the model using the circumference measurements collected during the setup operation as well as the new circumference measurements.

While the contoured line "L1" has been described as being a parabola, instead, the contoured line "L1" may be V-shaped. In such an implementation, the wrist or ankle is modeled as two cones axially aligned and merged together near each of their points. However, each of the cones has a linear taper and constant surface angle with respect to the axis of the cone. In contrast, a limb, particularly near the wrist or ankle, has a curved and somewhat parabolic shape. Thus, it may be desirable for the contoured line "L1" to have a rate of taper change, or apparent surface angle change that is not constant. In particular, it may be desirable for the rate of taper change to lessen near the minimum circumference "MC-1" and increase progressively outwardly from the minimum circumference as occurs in a parabola.

By way of yet another non-limiting example, the model of the three-dimensional surface of the limb 11 may be constructed using anatomical data. For example, the model may be created by scanning a representative human limb or combining multiple scans of limbs to create a composite model. Multiple models may be created for different genders, ages, heights, weights, a combination thereof, and the like. Further, a model may be created for each patient by scanning the limb 11 of the patient 230.

In FIG. 12, the contoured line "L1" is symmetric about the y-axis. Thus, the contoured line "L1" indicates the rate of change in the surface angle of the limb 11 is the same at locations equidistant from the minimum circumference "MC-1" along the longitudinal axis of the limb 11. However, this may not be the case. Because the rate of change of the surface angle of the patient's limb 11 is likely to be different and nonsymmetrical along the longitudinal axis of the limb 11 from the minimum circumference "MC-1" toward the direction toward the extremity (e.g., foot or hand) than in the opposite direction from the minimum circumference "MC-1," different mathematical equations or a different model may be used to model these portions of the limb 11. As mentioned above, the accelerometer value(s) may be used to determine the orientation of the device 10 so that whether the device 10 is above or below the minimum circumference "MC-1" may be determined.

Figure 8B:
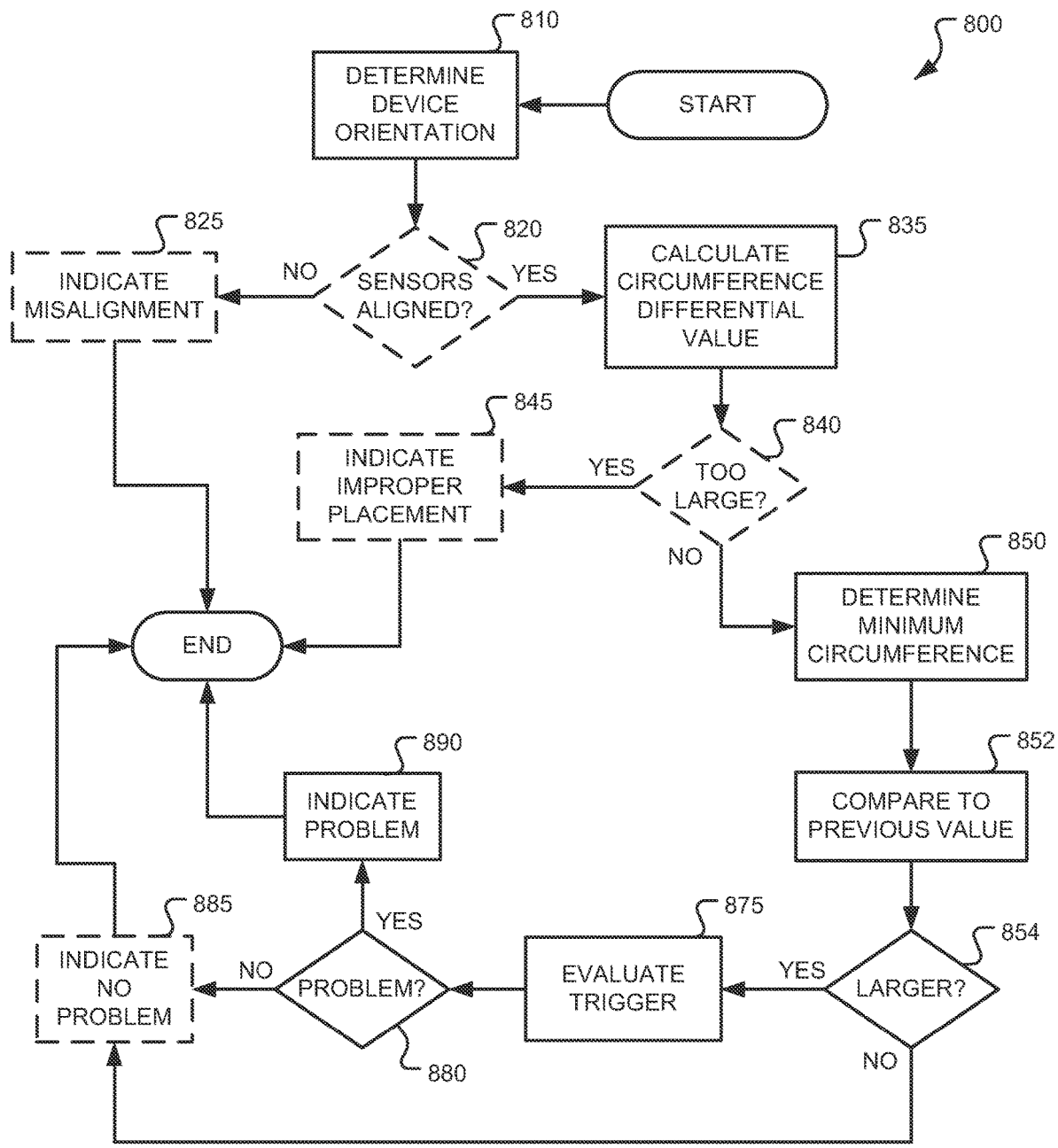
FIG. 8B is a flow diagram of a method of analyzing the patient data performed by the control system.

FIG. 8B is a flow diagram of the method 800 of analyzing the calculated values and accelerometer value(s) (and optionally the data obtained from the oximeter 420 and/or the heart rate sensor 415) optionally transferred to the control system 220 by the device 10. By way of a non-limiting example, the method 800 will be described as being performed by the database server 370 (see FIG. 3). However, in alternate embodiments, the method 800 may be performed by the device 10, the control system 220, and/or a combination thereof. The method 800 may be performed immediately after block 740 in the method 700. Alternatively, the method 800 may be performed after two or more transmissions are received from the device 10. By way of yet another non-limiting example, the method 800 may be performed at predetermined intervals.

For ease of illustration, the method 800 will be described with respect to the circumference measurements plotted as points "P1" and "P2" in FIG. 12. However, as is apparent to those of ordinary skill in the art, the method 800 may be performed with respect to more than a pair of circumference measurements.

In first block 810, the database server 370 determines an orientation of the device 10 when the "lit" analog signals used to determine the calculated values from which the circumference measurements plotted as the points "P1" and "P2" in FIG. 12 were collected. In block 810, the database server 370 performs orientation signal processing on the accelerometer value(s) transferred with the calculated values to determine the orientation of the device 10 on the limb 11. By way of a non-limiting example, an accelerometer with three orthogonal sensing elements detects static deflections in each of the sensing elements that may be used to determine gravitation direction and thus device orientation. Such orientation signal processing is known in the art and will not be described in detail. The database server 370 may store the orientation of the device 10.

In optional decision block 820, the database server 370 may determine whether the sensors 450, 455, and 460 were properly aligned with the optical gradient 1545. The calculated value for the sensor 455 may be used to verify the alignment of the emitter "E2" with the optical gradient 1545. For example, if the calculated value is within a predetermined range expected for the solid portion "GS" of the optical gradient 1545, the database server 370 determines the sensors 450, 455, and 460 were properly aligned with the optical gradient 1545. Otherwise, if the calculated value is not within the predetermined range expected for the solid portion "GS" of the optical gradient 1545, the database server 370 determines the sensors 450, 455, and 460 were improperly aligned.

The decision in optional decision block 820 is "YES" when the database server 370 determines the sensors 450, 455, and 460 were properly aligned with the optical gradient 1545. On the other hand, the decision in optional decision block 820 is "NO" when the database server 370 determines the sensors 450, 455, and 460 were improperly aligned with the optical gradient 1545.

When the decision in optional decision block 820 is "NO," in optional block 825, the database server 370 may indicate a misalignment occurred. Then, the method 800 terminates having failed to determine a final circumference value (or edema measure).

When the decision in optional decision block 820 is "YES," or the optional decision block 820 is omitted, in block 835, the database server 370 calculates a circumference differential value for the circumference measurements plotted as the points "P1" and "P2" in FIG. 12. As explained above, to calculate the circumference differential value, the database server 370 may calculate a first circumference measure for the sensor 450 based on the calculated value for the sensor 450 and a second circumference measure for the sensor 460 based on the calculated value for the sensor 460. For ease of illustration, the device 10 will be described as being in the orientation illustrated in FIGS. 13 and 17. However, this is not a requirement. When the device 10 is in this orientation, the sensor 460 is nearer an extremity (e.g., a hand or a foot) and is positioned below the sensor 450, which is farther away from the extremity. Thus, the sensor 450 may be characterized as being an upper sensor and the sensor 460 may be characterized as being a lower sensor. However, as is appreciated by those of ordinary skill in the art, the assignment of upper and lower are purely arbitrary and vary based upon the position of the patient's limb. By way of a non-limiting example, the circumference differential value may be calculated by subtracting the first circumference measure for the (upper) sensor 450 from the second circumference measure for the (lower) sensor 460.

If the circumference differential value is approximately zero, the sensors 450 and 460 are adjacent portions of the optical gradient 1545 having substantially equivalent reflectivity. Because the first and second gradient portions "G1" and "G2" are substantially aligned with one another, this means the sensors 450 and 460 are adjacent corresponding portions of the first and second gradient portions "G1" and "G2." The device 10 is illustrated in this configuration in FIG. 10B. This may indicate the device 10 is positioned approximately at the patient's wrist or ankle.

On the other hand, if the circumference differential value is greater than or less than zero, the sensors 450 and 460 are not adjacent corresponding portions of the first and second gradient portions "G1" and "G2." As will be described in greater detail below, the position of the sensors 450, 455, and 460 relative to the optical gradient 1545 varies with the circumference of the patient's limb 11. Further, the position of the sensors 450, 455, and 460 relative to the optical gradient 1545 along the transverse direction (indicated by the arrow "TD") may vary based upon the location of the device 10 on the patient's limb 11.

Figure 10C:
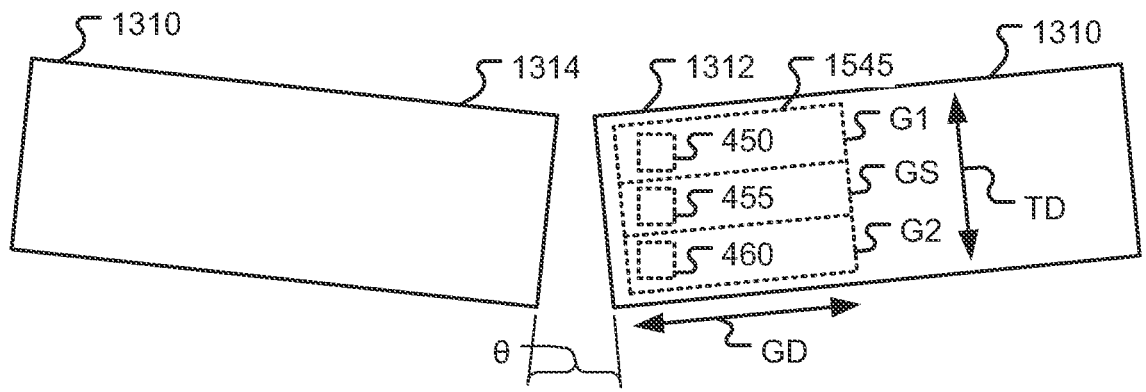
FIG. 10C is an illustration the device positioned on the patient's limb at a location below the minimum circumference of the patient's limb depicting the strap, optical gradient, and sensors that may be used to construct the device.

If the circumference differential value is greater than zero, the device 10 may be positioned above the patient's wrist or ankle. The device 10 is illustrated in this configuration in FIG. 10A. On the other hand, if the circumference differential value is less than zero, the device 10 may be positioned below the patient's wrist or ankle. The device 10 is illustrated in this configuration in FIG. 10C.

In decision block 840, the database server 370 determines whether the circumference differential value is too large, indicating improper placement of the device 10. By way of a non-limiting example, the database server 370 may determine the circumference differential value is too large if the circumference differential value is greater than a predetermined threshold value. The decision in decision block 840 is "YES" when the database server 370 determines the circumference differential value is too large. On the other hand, the decision in decision block 840 is "NO" when the database server 370 determines the circumference differential value is not too large.

When the decision in decision block 840 is "YES," in optional block 845, the database server 370 sends a message to the patient 230 to adjust the position of the device 10. Further, in optional block 845, the database server 370 may remove the calculated values from the patient record. Then, the method 800 terminates.

Because the circumference of the limb 11 varies along its longitudinal axis, to compare successive circumference measurements to one another directly, the circumference measurements must have been collected from nearly identical locations along the longitudinal axis of the limb 11. Because the device 10 may move along the longitudinal axis of the limb 11, it may not be possible to compare successive circumference measurements directly. Further, the patient 230 may inadvertently position the device 10 in different locations along the patient's limb between circumference measurements, which could contribute to measurement errors. However, as explained above, the model (e.g., the contoured line "L1") may be used to obtain the minimum circumference "MC-1" (or an estimate thereof) for the limb 11. The minimum circumference values obtained from successive circumference measurements may be compared directly because they are believed to be from the same location on the limb 11.

When the decision in decision block 840 is "NO," in block 850, the database server 370 determines a minimum circumference "MC-3" for the circumference measurements plotted as the points "P1" and "P2" in FIG. 12 and whether the minimum circumference "MC-3" indicates the size of the limb 11 has changed. As mentioned above, the database server 370 may create a lookup table using the pairs of circumference measurements used to create the model.

The database server 370 may use the lookup table to determine whether the minimum circumference "MC-3" and whether the circumference of the limb 11 has changed. For example, the database server 370 may determine the circumference of the limb 11 has not changed if the newly measured pair of circumference measurements (plotted as the points "P1" and "P2" in FIG. 12) includes a circumference measurement corresponding to the circumference measurement stored in the lookup table for a previously collected pair of circumference measurements, and the circumference differential value of the new pair of circumference measurements matches the circumference differential value stored for the same previously collected pair of circumference measurements. When this is the case, the minimum circumference "MC-1" associated with the previously collected pair of circumference measurements may be used as the minimum circumference "MC-3" for the new pair.

Similarly, the database server 370 may determine the circumference of the limb 11 has not changed if the newly measured pair of circumference measurements (plotted as the points "P1" and "P2" in FIG. 12) includes a circumference measurement between the circumference measurements stored in the lookup table for a first previously collected pair of circumference measurements and a second previously collected pair of circumference measurements, and the circumference differential value of the new pair of circumference measurements is between the circumference differential values stored for the first and second previously collected pairs of circumference measurements. When this is the case, the minimum circumference "MC-1" associated with the previously collected pair of circumference measurements may be used as the minimum circumference "MC-3" for the new pair. The position of the new pair on the contoured line "L1" may be determined using interpolation (e.g., linear interpolation) between the first and second previously collected pairs of circumference measurements.

However, the database server 370 may determine the circumference of the limb 11 has changed if the newly measured pair of circumference measurements (plotted as the points "P1" and "P2" in FIG. 12) includes a circumference measurement corresponding to the circumference measurement stored in the lookup table for a previously collected pair of circumference measurements, but the circumference differential value of the new pair of circumference measurements does not match the difference value stored for the same previously collected pair of circumference measurements. Similarly, the database server 370 may determine the circumference of the limb 11 has changed if the newly measured pair of circumference measurements includes a circumference measurement between the circumference measurements stored in the lookup table for a first previously collected pair of circumference measurements and a second previously collected pair of circumference measurements, but the circumference differential value of the new pair of circumference measurements is not between the circumference differential values stored for the first and second previously collected pairs of circumference measurements.

Referring to FIG. 12, if the limb 11 has swelled but its shape has remained substantially unchanged, the swollen limb may be modeled by a contoured line "L3," which has the same shape as the contoured line "L1," but is shifted upwardly on the y-axis relative to the contoured line "L1." In this example, the point "P1" is aligned vertically with the point "A7" and the point "P2" is aligned vertically with the point "A8." Therefore, the circumference differential value of the new pair of circumference measurements (plotted as the points "P1" and "P2") is the same as the circumference differential value stored in the lookup table for the previously collected pair of circumference measurements (plotted as the points "A7" and "A8"). However, a first circumference measurement (plotted as the point "P1") of the new pair is larger than the corresponding first circumference measurement (plotted as the point "A7") of the previously collected pair. Similarly, a second circumference measurement (plotted as the point "P2") of the new pair is larger than the corresponding second circumference measurement (plotted as the point "A8") of the previously collected pair. Thus, no matter which of the circumference measurements of the previously collected pair are stored in the lookup table, the lookup table will indicate the limb 11 has swollen when corresponding circumference measurements of the new and previously collected pairs are compared to one another.

Referring to FIG. 12, if swelling in the limb 11 has reduced but its shape has remained substantially unchanged, the limb may be modeled by a contoured line having the same shape as the contoured line "L1," but shifted downwardly on the y-axis relative to the contoured line "L1." The circumference differential value of a new pair of circumference measurements will be the same as the circumference differential value stored in the lookup table for a previously collected pair of circumference measurements. However, a first circumference measurement of the new pair will be smaller than the corresponding first circumference measurement of the previously collected pair. Similarly, a second circumference measurement of the new pair will be smaller than the corresponding second circumference measurement of the previously collected pair. Thus, no matter which of the circumference measurements of the previously collected pair are stored in the lookup table, the lookup table will indicate swelling in the limb 11 has reduced when corresponding circumference measurements of the new and previously collected pairs are compared to one another.

When the database server 370 determines the size of the limb 11 has changed, the database server 370 generates a contoured line (e.g., the contoured line "L3"), and uses the contoured line to determine the minimum circumference (e.g., the minimum circumference "MC-3") of the limb 11.

In block 852, the database server 370 compares the previously obtained minimum circumference "MC-1" to the newly measured minimum circumference (e.g., the minimum circumference "MC-3").

In decision block 854, the database server 370 determines whether the newly measured minimum circumference (e.g., the minimum circumference "MC-3") is larger than the previously obtained minimum circumference "MC-1," indicating the limb 11 has swollen. The decision in decision block 854 is "YES" when the newly measured minimum circumference (e.g., the minimum circumference "MC-3") is larger than the previously obtained minimum circumference "MC-1." On the other hand, the decision in decision block 854 is "NO" when the newly measured minimum circumference (e.g., the minimum circumference "MC-3") is not larger than the previously obtained minimum circumference "MC-1."

When the decision in decision block 854 is "NO," the database server 370 advances to block 885.

When the decision in decision block 854 is "YES," in block 875, the database server 370 analyzes one or more triggers to determine whether any have been satisfied such that a message is be sent to the patient 230 (e.g., the message 225 illustrated in FIG. 2), the support person 330, and/or the caregiver 332. For example, a trigger may have been entered into the website 217 indicating that if the limb 11 swells by more than a trigger threshold value, the message 225 (see FIG. 2) is to be sent to the patient 230. In block 875, the database server 370 determines by how much the limb 11 has swelled and compares that amount to the trigger threshold value.

By way of example, in block 875, the database server 370 may determine an amount of change and/or a rate of change. In block 875, the database server 370 may try to identify a trend indicative of a problem. For example, if the minimum circumference values appear to be increasing, the patient 230 may be experiencing a medical problem. In block 875, the database server 370 may determine an amount by which edema in the limb 11 has changed.

In decision block 880, the database server 370 determines whether one or more triggers are satisfied indicating a problem. The decision in decision block 880 is "YES" when the database server 370 determines one or more triggers are satisfied. On the other hand, the decision in decision block 880 is "NO" when the database server 370 determines none of the triggers are satisfied.

When the decision in decision block 880 is "NO," in optional block 885, the database server 370 may send a notification indicating no problem has been detected to the device 10, the patient desktop computer 335, the patient cellular telephone 350, the patient portable computer 355, and the like to be viewed by patient 230. The notification may be viewable on the website 217 (see FIG. 2). Optionally, the database server 370 may send a notification indicating no problem has been detected to the computing device 310 to be viewed by the support person 330 and/or to the computing device 315 to be viewed by the caregiver 332. Any such notifications may be viewable on the website 217 (see FIG. 2). Then, the method 800 terminates.

When the decision in decision block 880 is "YES," in block 890, the database server 370 may send a notification indicating a problem has been detected to the device 10, the patient desktop computer 335, the patient cellular telephone 350, the patient portable computer 355, and the like to be viewed by patient 230. The notification may be viewable on the website 217 (see FIG. 2). Optionally, the database server 370 may send a notification indicating a problem has been detected to the computing device 310 to be viewed by the support person 330 and/or to the computing device 315 to be viewed by the caregiver 332. Any such notifications may be viewable on the website 217 (see FIG. 2). Instructions may be associated with the trigger and included in the message sent to the patient 230, the support person 330, and/or the caregiver 332. The instructions may include a predefined treatment plan. Then, the method 800 terminates.

Figure 11:
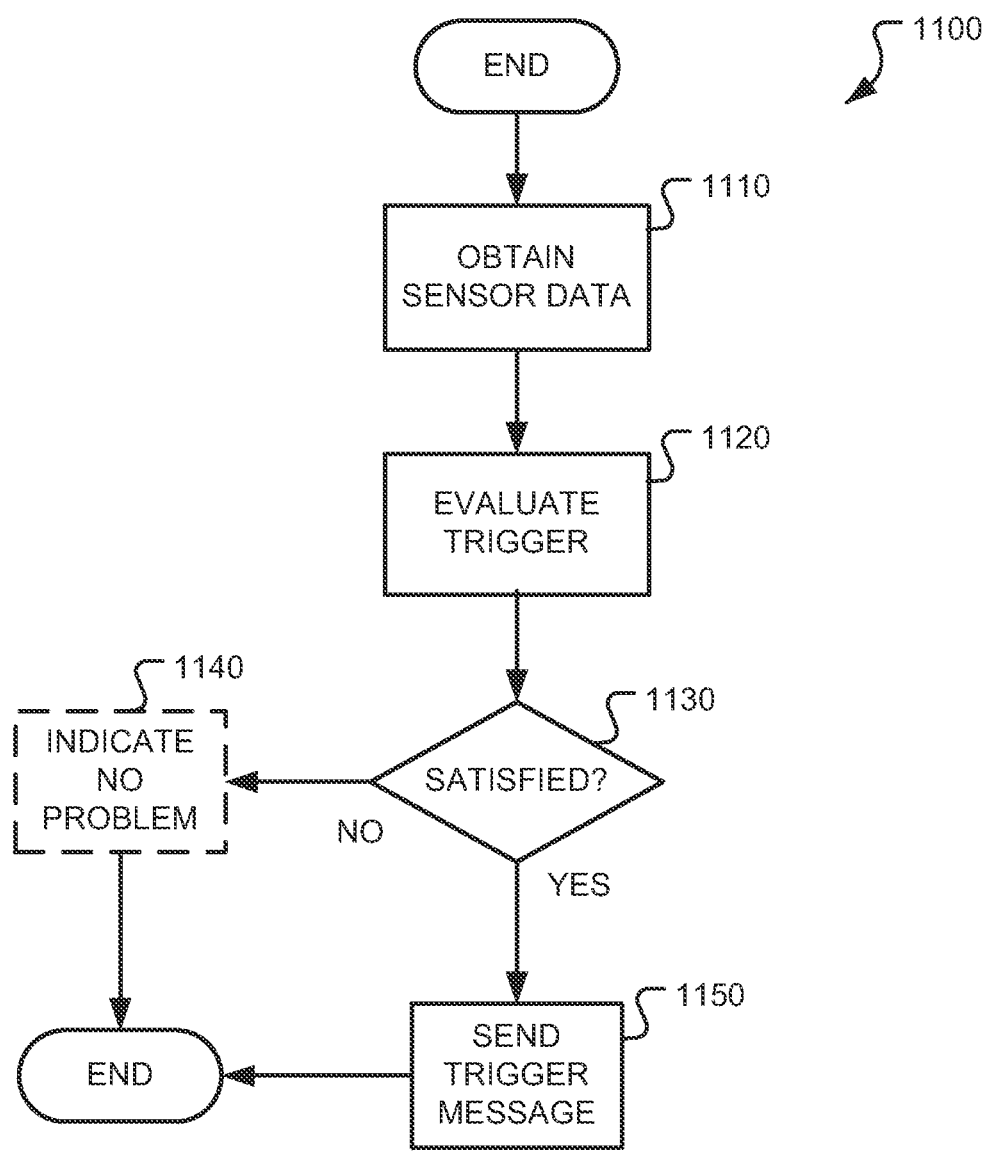
FIG. 11 is a flow diagram of a method of analyzing the patient data received from the device worn on a patient's limb performed by the control system.

FIG. 11 is a flow diagram of a method 1100 of processing triggers specified for sensors other than the sensors 450, 455, and 460. The method 1100 may be performed by the device 10, the control system 220, and/or a combination thereof. For ease of illustration, the method 1100 will be described as being performed by the database serve 370. As mentioned above, the patient 230, the support person 330, and/or the caregiver 332 may use the website 217 to specify trigger conditions (e.g., threshold values) that trigger messages to the patient 230, the support person 330, and/or the caregiver 332. The method 1100 may be used with the accelerometer values(s) obtained from the accelerometer 405, oxygen amounts obtained from the oximeter 420, and/or heart rate values obtained from the heart rate sensor 415. Further, the method 1100 may be used with the calculated values obtained from the sensors 450, 455, and 460 combined with the data from one or more of the other sensors.

In the first block 1110, the database server 370 obtains the relevant sensor data.

In block 1120, the database server 370 analyzes the sensor data relative to one or more triggers to determine whether any of the triggers have been satisfied such that a trigger message is to be sent to the patient 230 (e.g., the message 225 illustrated in FIG. 2), the support person 330, and/or the caregiver 332. For example, a trigger may have been entered into the website 217 indicating that if the patient's physical activity drops below a specified level, a trigger message is to be sent to the patient 230, the support person 330, and/or the caregiver 332 reporting unusual inactivity. By way of another example, increased peripheral edema measurements might trigger a predetermined prescribed treatment plan that could include increasing a dosage of a diuretic or other medication. By way of yet another example, a combination of sensor measurements (e.g., measurements indicating increased edema and reduced activity) may trigger additional stress testing, automated patient symptom questions, a nurse to call or messages to setup an appointment with a healthcare provider. In block 1120, the database server 370 may try to identify a trend indicative of a problem.

In decision block 1130, the database server 370 determines whether one or more triggers are satisfied indicating a problem. The decision in decision block 1130 is "YES" when the database server 370 determines one or more triggers are satisfied. On the other hand, the decision in decision block 1130 is "NO" when the database server 370 determines none of the triggers are satisfied.

When the decision in decision block 1130 is "NO," in optional block 1140, the database server 370 may send a notification indicating no problem has been detected to the device 10, the patient desktop computer 335, the patient cellular telephone 350, the patient portable computer 355, and the like to be viewed by patient 230. The notification may be viewable on the website 217 (see FIG. 2). Optionally, the database server 370 may send a notification indicating no problem has been detected to the computing device 310 to be viewed by the support person 330 and/or to the computing device 315 to be viewed by the caregiver 332. Any such notifications may be viewable on the website 217 (see FIG. 2). Then, the method 800 terminates.

When the decision in decision block 1130 is "YES," in block 1150, the database server 370 may send a trigger message indicating a problem has been detected to the device 10, the patient desktop computer 335, the patient cellular telephone 350, the patient portable computer 355, and the like to be viewed by patient 230. The trigger message may be viewable on the website 217 (see FIG. 2). Optionally, the database server 370 may send a trigger message indicating a problem has been detected to the computing device 310 to be viewed by the support person 330 and/or to the computing device 315 to be viewed by the caregiver 332. Any such trigger messages may be viewable on the website 217 (see FIG. 2). Instructions may be associated with the trigger and included in the message sent to the patient 230, the support person 330, and/or the caregiver 332. For example, the trigger message may instruct the patient 230 to engage in a particular physical activity (e.g., a stress test) for the purposes of collecting patient data during the physical activity. The collection of such data may be coordinated using the website 217. As the patient 230 engages in the particular physical activity, the device 10 collects data (using the accelerometer 405, the heart rate sensor 415, the oximeter 420, the sensor 450, the sensor 455, and/or the sensor 460) and transfers the data collected to the control system 220. Then, the method 1100 terminates.

Feedback may be used to improve the system 200 using retrospective analysis. A website or telephone interaction, for example, may be used to provide a convenient means of feeding information back to the control system 220 regarding decompensation events, if any occur. The patient history can be reviewed to improve of the performance of the control system 220. In cases where the caregiver 332 (or other healthcare professional) is available by telephone, the system 200 may be used to trigger prospective interaction with the patient 230 that the caregiver 332 may enter into the patient record. In this manner, the system 200 may acquire additional information that may be used to improve the ability of the system to recognize problems. Further, the system 200 may use such information to provide an earlier indication of a problem that may be reversible by simple measures, such as improved treatment plan compliance, additional medication, reduced salt intake, and the like, which may be implemented before the patient 230 requires emergency healthcare system intervention.

Device 10

As described above, FIG. 4 illustrates the circuit 400 that may be used to construct the device 10. Referring to FIGS. 13-18 other components that may be used to construct the device 10 will be described.

Turning to FIG. 17, in the embodiment illustrated, the circuit 400 is mounted on a substrate 1505 (e.g., a printed circuit board) housed inside a two-part electronics enclosure 1335. A removable battery 1620 may provide power to the circuit 400. An insulator 1805 may be positioned adjacent the circuit 400 to allow the battery 1620 to be changed without contacting the circuit 400. The electronics enclosure 1335 includes a body portion 1540 and a transparent cover 1810. The body portion 1540 may include a compliant, elastomeric portion 1535 that is positioned against the patient's limb 11 when the device 10 is worn. The body portion 1540 is substantially fluid tight to prevent fluid ingress. The electronics enclosure 1335 may be positioned inside the frame member 1337 having a hook 1330 spaced part from the guide portion 1315.

Turning to FIG. 13, in the embodiment illustrated, the first end portion 1312 of the strap 1310 is connected to the frame member 1337 surrounding the electronics enclosure 1335 by the tensioning member 1320 and the second end portion 1314 of the strap 1310 is connected to the guide portion 1315 of the frame member 1337.

The first end portion 1312 of the strap 1310 extends around the tensioning member 1320 and is affixed to itself. For example, the first end portion 1312 of the strap 1310 may be looped around the tensioning member 1320, folded back on itself, and affixed in place by an adhesive material 1345. A guide 1340 spaced apart from the tensioning member 1320 may also be adhered to the first end portion 1312 of the strap 1310 by the adhesive material 1345. The guide 1340 may be configured to limit lateral movement of the first end portion 1312 of the strap 1310 to help maintain the optical gradient 1545 adjacent the sensors 450, 455, and 460, even when the device 10 is positioned on a portion of the patient's limb 11 (see FIG. 1) at a location of extreme taper. By way of a non-limiting example, the adhesive material 1345 may include a double stick adhesive, such as 3M 5952 (3M, St Paul, Minn.) or similar adhesive material.

The second end portion 1314 of the strap 1310 is removably or repositionally affixed to itself by a different adhesive tape 1325, such as 3M 9425 or similar adhesive material. The second end portion 1314 of the strap 1310 is looped around the guide portion 1315 of the frame member 1337, folded back on itself, and removably fixed in place by the adhesive tape 1325. The second end portion 1314 of the strap 1310 may be repositioned to adjust the length of the strap 1310 to allow for a large range of circumference changes and for use with a variety of small and large limbs.

The strap 1310 is flexible, substantially inelastic, and resists stretching when worn by the patient 230 (see FIG. 1). By way of a non-limiting example, the strap 1310 may be constructed from an inelastic material, such as Tyvek (Dupont, Wilmington, Del.) or other similar material.

Figure 15:
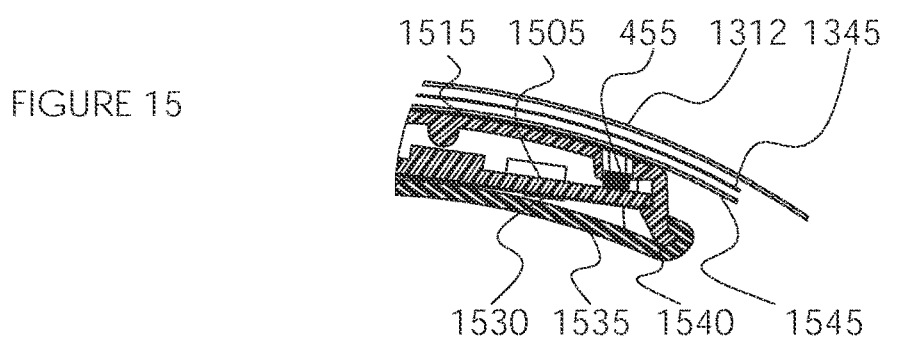
FIG. 15 is an enlarged cross-sectional view of a portion of the device cross-sectioned along the A-A line of FIG. 13.
Figure 16:
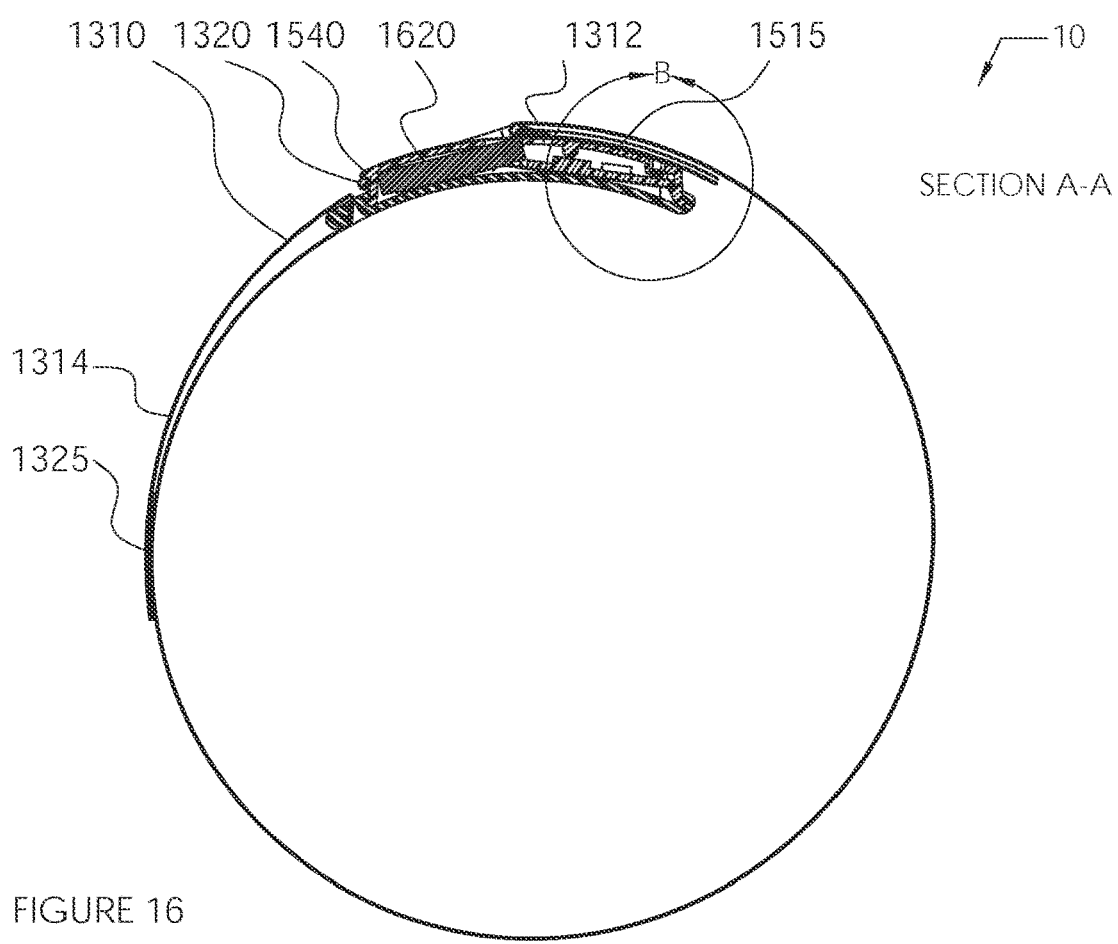
FIG. 16 is cross-sectional view of the device cross-sectioned along the A-A line of FIG. 13.

Referring to FIG. 15, as mentioned above, the sensor portion 1515 of the electronics enclosure 1335 extends under the first end portion 1312 of the strap 1310 and the optical gradient 1545 is positioned on the first end portion 1312 of the strap 1310 to face the sensor portion 1515 of the electronics enclosure 1335. The emitter "E1" and detector "D1" of the sensor 450, the emitter "E2" and detector "D2" of the sensor 455, and the emitter "E3" and detector "D3" of the sensor 460 are positioned on the sensor portion 1515 of the electronics enclosure 1335 with the emitters and detectors facing toward the optical gradient 1545 on the first end portion 1312 of the strap 1310.

The tensioning member 1320 may be coupled to the hook 1330 of the frame member 1337. Tension in the tensioning member 1320 pulls the first end portion 1312 toward the electronics enclosure 1335 to thereby impart tension in the strap 1310, which may hold the strap 1310 snuggly against the limb 11. Further, the tensioning member 1320 may help maintain the position of the gradient surface 1545 adjacent to the sensor portion 1515 of the electronics enclosure 1335. This tensioning member 1320 allows the first and second end portions 1312 and 1314 of the strap 1310 to skew relative to one another (to define the angle "θ" illustrated in FIGS. 10A and 10C) and allows the strap to follow the surface of the limb 11.

At least a portion of the sensor portion 1515 of the electronics enclosure 1335 may be transparent to the light emitted by the emitters "E1," "E2," and "E3" (e.g., red and infrared radiation having a wavelength between about 600 nm to about 1000 nm). In the embodiment illustrated, the transparent cover 1810 that allows light emitted by the emitters "E1," "E2," and "E3" to pass therethrough to illuminate the optical gradient 1545. A portion of the light emitted by the emitters "E1," "E2," and "E3" is reflected back toward the detectors "D1," "D2," and "D3" positioned inside the sensor portion 1515 of the electronics enclosure 1335. The reflected light passes through the transparent cover 1810 and into the sensor portion 1515 of the electronics enclosure 1335 where it is detected by the detectors "D1," "D2," and "D3."

The amount of light reflected back toward the sensor portion 1515 is proportional to the position of the detectors "D1" and "D3" relative to the gradient portions "G1" and "G2," respectively. The light sensed by the detectors "D1" and "D3" may be correlated to the position of the device 10 on the limb 11.

Optionally, the device 10 may include a display (not shown), such as a liquid crystal display, configured to display messages sent to the device.

In an alternate embodiment, referring to FIG. 4, the radio 430 and the antenna 425 are omitted from the circuit 400. Instead, referring to FIG. 18, in a device 1700, the circuit 400 is configured to communicate via a wired connection 1710 with an external computing device (e.g., the patient desktop computer 335, the patient cellular telephone 350, the patient portable computer 355, and the like). The wired connection 1710 includes a cable 1715 connected at one end to the circuit 400 and at the opposite end to a connector 1720 (e.g., a universal serial bus connector). The connector 1720 may be configured to receive power from the external computing device. In such embodiments, the circuit 400 may be powered by the wired connection 1710, instead of the battery 1620.

In another alternate embodiment, the device 10 may be configured to store measurements (and other data), and display information directly to the patient 230. In such an embodiment, the device 10 may analyze the stored data, or alternatively, be connected to an external communications device configured to transfer the data for analysis by an external computing device (e.g., the database server 370). When the analysis is completed, the results may be transferred to the device for display thereby.

The width of the strap 1310 may be selected such that the strap intimately and contiguously follows the surface of the limb 11 and at the same time properly places the sensors 450, 455, and 460 relative to the optical gradient 1545. By way of a non-limiting example, the strap 1310 may be about 25 mm wide. Further, the sensor 450 may be spaced about 20 mm from the sensor 460.

Declines in patient activity level have also been found to correlate to impending decompensation. Therefore, the accelerometer 405 may be used to measuring patient activity and transmit such information to the control system 220 for analysis thereby to detect trends in general patient activity.

The control system 220 may also detect falls and recognize leg orientation to better understand variations in patient activity. The control system 220 may be configured to recognize a substantial variation in patient activity alone as a predictor of a medical problem. In response to detecting a substantial variation in patient activity, the control system 220 may send a message to the patient 230 (via the patient desktop computer 335, the patient cellular telephone 350, the patient portable computer 355, and the like), the support network 210 (e.g., via the computing device 310), and/or the healthcare system 205 (e.g., via the computing device 315). Further, the circuit 400 may be modified to include sensors for detecting other physiological parameters such as impedance, respiration, electrocardiogram ("ECG"), and or pulse velocity non-invasive blood pressure ("NIBP"). Physiological parameters sensed by the circuit 400 may be stored, analyzed, and displayed locally on the device 10, or communicated to an external computing device.

The control system 220 may send instructions to the device 10. For example, the control system 220 may instruct the device 10 to collect measurements from particular sensors, change the schedule (e.g., intervals) when measurements are collected, display status information, modify (e.g., update) local software programs, and the like.

The control system 220 may route messages to the patient 230, the support person 330, and/or the caregiver 332 in a scheduled or event driven manner. Not all significant heart failure symptoms are objective, physiological measurements. Scheduled messages sent to the patient (e.g., sent via the patient cellular telephone 350) including questions regarding breathlessness, as an example, might be used to gather information useful for generating a trend baseline of the patient's condition. Event driven messages might request that the patient 230, as an example, perform particular actions (e.g., perform a walking stress test) to characterize the significance of changes observed in the patient's physiological conditions. The control system 220 may analyze data as it is received (in view of the patient record), route messages, and initiate actions as required.

Thus, the system 200 implements a feedback or control loop is created in which the control system 220 may immediately recognize a swelling trend in the patient's limb 11. A heart failure patient can substantially affect the progression of the disease by compliance with a treatment plan, which may include medication, diet, and exercise. The system 200 may reinforce compliance by providing a means for patients to connect with each other by messaging, voice, and chat room options.

While the sensors 450, 455, and 460 have been described as being light sensors, those of ordinary skill in the art appreciate that embodiments may be constructed using other types of sensors, such as linear variable resistors, rotary variable resistors, pressure sensors, strain sensors, magnetoresistive circuits, conductive fabric, conductive elastomers, and the like. Additionally, embodiments may be constructed using sensors that measure capacitance, inductance, magnetorestrictive, Hall Effect, optical pattern encoding, optical path measurement, light loss bending constructions, piezo effect, eddy current, ultrasound, and/or radar.

The device 10 has been described as including sensors 450, 455, and 460 configured for use with an optical gradient 1545. However, other methods may be used to determine whether the distance around the limb 11 has changed. For example, sensors configured to sense strain or pressure may be used.

Further, the system 200 may be configured to receive circumference measurements from devices other than the device 10 and use those measurements to evaluate the circumference of the patient's limb.

Computing Device

Figure 19:
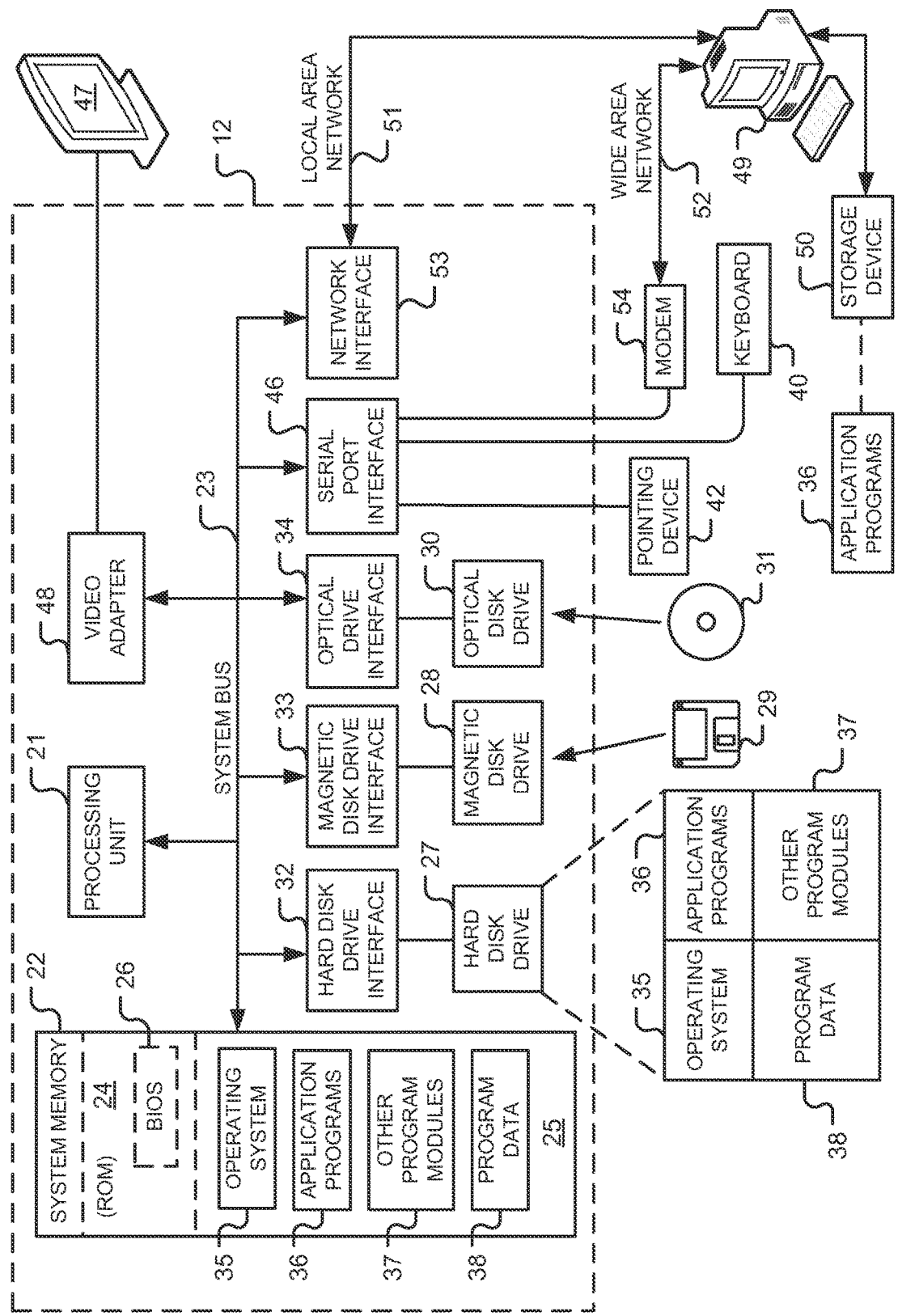
FIG. 19 is a diagram of a hardware environment and an operating environment in which one or more of the computing devices of the system of FIG. 1 may be implemented.

FIG. 19 is a diagram of hardware and an operating environment in conjunction with which implementations of the database server 370, the patient desktop computer 335, the patient cellular telephone 350, the patient portable computer 355, the support computing device 310, the caregiver computing device 315, and the web server 318 may be practiced. The description of FIG. 19 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that implementations may be practiced with other computer system configurations, including hand-held devices, multi-processor systems, microprocessor-based or programmable consumer electronics, network PCs, minicomputers, mainframe computers, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 19 includes a general-purpose computing device in the form of a computing device 12. The database server 370, the patient desktop computer 335, the patient cellular telephone 350, the patient portable computer 355, the support computing device 310, the caregiver computing device 315, the web server 318 may each be implemented using one or more computing devices like the computing device 12.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like.

The computing device 12 may be a conventional computer, a distributed computer, or any other type of computer.

The system bus 23 may be any of several types of bus structures including a memory bus or memory controller, a peripheral bus, and a local bus using any of a variety of bus architectures. The memory 410 (illustrated FIG. 4) may be substantially similar to the system memory 22. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types physical feedback (e.g., a force feed back game controller).

The input devices described above are operable to receive user input and selections. Together the input and display devices may be described as providing a user interface. The input devices may be used to receive information from the patient 230, the support person 330, the caregiver 332, and the like. The user interface may be used to display messages (e.g., notifications and alters) to the patient 230, the support person 330, the caregiver 332, and the like.

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 10 include a local-area network (LAN) 51 and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

The memory of the database server 370 stores computer executable instructions that when executed by one or more processors cause the one or more processors to perform all or portions of the methods 700, 750, 800, and/or 1100.

The memory 410 of the device 10 stores processor executable instructions that when executed by the processor 435 cause the processor to perform all or portions of the methods 500, 600, 650, 750, 800, and/or 1100.

Any of the instructions described above, including the instructions of stored by the memory of the database server 370 and in the memory 410 of the device 10, may be stored on one or more non-transitory computer-readable media.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A computer-implemented method of managing heart failure, comprising:
   receiving, at a computing device, feedback information comprising sensor data of a current state of a patient from a plurality of sensors of a patient monitoring device associated with a device identifier, the patient monitoring device measuring distances at one or more locations around a limb of the patient;
   generating, by the computing device, a model of the limb of the patient based at least on one or more measured circumferences of the limb recorded in a patient record associated with a patient monitoring device, the one or more measured circumferences of the limb comprising a minimum circumference of the limb;
   determining, by the computing device, whether the sensor data satisfies one or more trigger conditions based at least on a comparison of the feedback information and reference information associated with the patient, the feedback information comprising a measured circumference of the limb and the reference information comprising the minimum circumference of the limb recorded in the patient record associated with the patient monitoring device;
   for each of the one or more trigger conditions determined to be satisfied, generating, by the computing device, an event driven message comprising instructions to the patient based at least on the current state of the patient and the patient record; and
   displaying, by the computing device, the event driven message on at least one of the patient monitoring device associated with the device identifier and an external computing device displayable thereby to at least one of the patient, a caregiver, and a support person.

2. The computer-implemented method of claim 1, wherein satisfaction of at least a first trigger condition of the one or more trigger conditions indicates the patient has edema.

3. The computer-implemented method of claim 1, wherein satisfaction of at least a first trigger condition of the one or more trigger conditions indicates the patient is trending toward decompensation.

4. The computer-implemented method of claim 1, wherein the sensor data comprises data collected from at least one of a heart rate sensor, an oximeter, an accelerometer, and a sensor configured to detect a distance around the limb of the patient.

5. The computer-implemented method of claim 1, wherein the event driven message further comprises instructions to be executed by the patient to message additional patients via the external computing device.

6. The computer-implemented method of claim 1, further comprising:
   calculating, by the computing device, a digital signal value based at least on the sensor data; and
   determining, by the computing device, a circumference of the limb based at least on the digital signal value and the model of the limb.

7. A computer-implemented method, comprising:
   obtaining, at a computing device, from a patient monitoring device associated with a device identifier, a plurality of measurements of distances at one or more locations around a limb of a patient, the plurality of measurements associated with the patient monitoring device, the plurality of measurements of distances comprising a minimum circumference of the limb;
   generating, by the computing device, a trend baseline based at least on the plurality of measurements of the distances around the limb of the patient;
   obtaining, at the computing device, from the patient monitoring device, at least one new measurement of a distance around the limb of the patient, the at least one new measurement associated with the patient monitoring device;
   receiving, at the computing device, reference information comprising the trend baseline and a swelling threshold value of the limb;
   providing, via a user interface, to at least one of the patient, a caregiver, and a support person, the reference information;
   determining, by the computing device, whether the patient's limb has swelled by more than the swelling threshold value based at least on the trend baseline and the at least one new measurement of the distance around the patient's limb; and
   if it is determined the patient's limb has swelled by more than the swelling threshold value, displaying, by the computing device, a message associated with the swelling threshold value, on at least one of the patient monitoring device associated with the device identifier and an external computing device displayable thereby to at least one of the patient, the caregiver, and the support person indicating the patient's limb has swelled by more than the swelling threshold value.

8. The computer-implemented method of claim 7, wherein the message comprises instructions to be executed by the patient based at least on the trend baseline and the at least one new measurement.

9. The computer-implemented method of claim 8, wherein the instructions comprise a predefined treatment plan.

10. The computer-implemented method of claim 9, wherein the predefined treatment plan comprises an instruction to modify a dosage of at least one medication.

11. The computer-implemented method of claim 7, further comprising:
generating, by the computing device, a model of the limb of the patient based at least on the plurality of measurements of distances around the limb;
receiving, at the computing device, sensor data from the patient monitoring device; and
determining, by the computing device, a measurement of the distance around the limb of the patient based at least on the model of the limb and the sensor data.

12. The computer-implemented method of claim 7, wherein the minimum circumference corresponds to a measurement at a wrist or an ankle of the patient.

13. The computer-implemented method of claim 12, further comprising:
determining, by the computing device, a circumference differential value based at least on the plurality of measurements of distances around the limb; and
if the circumference differential value is greater than zero, determining, by the computing device, that a position of the patient monitoring device is above the wrist or the ankle.

14. One or more non-transitory computer-readable media storing computer-executable instructions that upon execution cause one or more computing devices to perform acts comprising:
receiving feedback information comprising sensor data of a current state of a patient from a plurality of sensors of a patient monitoring device associated with a device identifier, the patient monitoring device measuring distances at one or more locations around a limb of the patient;
generating a model of the limb of the patient based at least on one or more measured circumferences of the limb, the one or more measured circumferences of the limb comprising a minimum circumference of the limb;
determining whether the sensor data satisfies one or more trigger conditions based at least on a comparison of the feedback information and reference information associated with the patient, the feedback information comprising a measured circumference of the limb and the reference information comprising the minimum circumference of the limb recorded in a patient record associated with the patient monitoring device;
for each of the one or more trigger conditions determined to be satisfied, generating an event driven message comprising instructions to the patient based at least on the current state of the patient and the patient record; and
displaying the event driven message on at least one of the patient monitoring devices associated with the device identifier and an external computing device displayable thereby to at least one of the patient, a caregiver, and a support person.

15. The one or more non-transitory computer-readable media of claim 14, wherein satisfaction of at least a first trigger condition of the one or more trigger conditions indicates the patient has edema.

16. The one or more non-transitory computer-readable media of claim 14, wherein satisfaction of at least a first trigger condition of the one or more trigger conditions indicates the patient is trending toward decompensation.

17. The one or more non-transitory computer-readable media of claim 14, wherein the sensor data comprises data collected from at least one of a heart rate sensor, an oximeter, an accelerometer, and a sensor configured to detect a distance around the limb of the patient.

18. The one or more non-transitory computer-readable media of claim 14, wherein the instructions include modifying a dosage of at least one medication.

19. The one or more non-transitory computer-readable media of claim 14, the acts further comprising:
calculating a digital signal value based at least on the sensor data; and
determining a circumference of the limb based at least on the digital signal value and the model of the limb.

20. The one or more non-transitory computer-readable media of claim 14, the acts further comprising:
generating a trend baseline based at least on the one or more measured circumferences of the limb;
obtaining, from the patient monitoring device, at least one new measurement of a distance around the limb of the patient, the at least one new measurement associated with the patient monitoring device;
receiving reference information comprising the trend baseline and a swelling threshold value of the limb;
providing, via a user interface of at least one of the patient monitoring devices associated with the device identifier and an external computing device, the reference information;
determining whether the patient's limb has swelled by more than the swelling threshold value based at least on the trend baseline and the at least one new measurement of the distance around the patient's limb; and
if it is determined the patient's limb has swelled by more than the swelling threshold value, displaying an additional message associated with the swelling threshold value, on at least one of the patient monitoring devices associated with the device identifier and an external computing device displayable thereby to at least one of the patient, the caregiver, and the support person indicating the patient's limb has swelled by more than the swelling threshold value.

* * * * *